(12) United States Patent
Coleman et al.

(10) Patent No.: US 8,099,298 B2
(45) Date of Patent: Jan. 17, 2012

(54) GENETIC DATA ANALYSIS AND DATABASE TOOLS

(75) Inventors: Howard C Coleman, Seattle, WA (US);
Jessica Oesterheld, Bath, ME (US);
Robert D Patterson, Lexington, WA (US)

(73) Assignee: Genelex, inc, Seattle, WA (US)

( * ) Notice: Subject to any disclaimer, the term of this patent is extended or adjusted under 35 U.S.C. 154(b) by 978 days.

(21) Appl. No.: 12/031,327

(22) Filed: Feb. 14, 2008

(65) Prior Publication Data

US 2009/0094059 A1  Apr. 9, 2009

Related U.S. Application Data

(60) Provisional application No. 60/901,528, filed on Feb. 14, 2007, provisional application No. 61/026,724, filed on Feb. 6, 2008.

(51) Int. Cl.
*G06Q 40/00* (2006.01)
(52) U.S. Cl. ................................. 705/2; 705/3
(58) Field of Classification Search .................... 705/2–3
See application file for complete search history.

(56) References Cited

U.S. PATENT DOCUMENTS

| | | | |
|---|---|---|---|
| 5,960,411 A | 9/1999 | Hartman | |
| 6,063,026 A | 5/2000 | Gill-Garrison | |
| 6,968,513 B1 | 11/2005 | Rinebold et al. | |
| 7,054,755 B2 | 5/2006 | O'Reilly | |
| 7,058,616 B1 | 6/2006 | Larder | |
| 7,089,498 B1 | 8/2006 | Rathjen | |
| 7,266,839 B2 | 9/2007 | Bowers | |
| 2002/0049772 A1 | 4/2002 | Rienhoff | |
| 2003/0104453 A1 | 6/2003 | Pickar | |
| 2003/0135096 A1 | 7/2003 | Dodds | |
| 2004/0088191 A1 | 5/2004 | Holden | |
| 2004/0132771 A1* | 7/2004 | Babcock et al. | 514/311 |
| 2004/0197813 A1 | 10/2004 | Hoffman | |
| 2006/0289019 A1 | 12/2006 | Marchand | |
| 2009/0215812 A1* | 8/2009 | Bedrosian et al. | 514/291 |

OTHER PUBLICATIONS

Evans WE and MV Relling. 1999. Pharmacogenetics: translating functional genomics into rational therapeutics. Science 286:487-91.
Ichikawa Y. 2000. Single nucleotide polymorphism to disclose severe side-effects or proper dosage for each patient. Internal Med 39:523-24.
Philips KA et al. 2001. Potential role of pharmacogenomics in reducing adverse drug reactions: a systematic review. JAMA 286 (18): 2270-79.

(Continued)

*Primary Examiner* — Robert Morgan
*Assistant Examiner* — Reginald R Reyes
(74) *Attorney, Agent, or Firm* — K. Karel Lambert; Lambert Patent Services, LLC

(57) ABSTRACT

A computerized tool and method for delivery of pharmacogenetic and pharmacological information, comprising a core system having algorithms and databases for storing, collating, accessing, cross-referencing, and interpreting genetic and pharmacologic data, with a graphical user interface for a client network of providers of laboratory genetic testing services to access the core services under contract. The system includes "paypoints" in support of improved business models. Included are mechanisms for 'pass through' third party and insurance reimbursement for interpretive reports, insurance reimbursement for on-line access to pharmacogenetic information at the point of care, tools for market segmentation, and a conversion tool for capturing new subscribers. Also disclosed are tools and predictive algorithms for preventing drug-drug and drug-gene adverse drug reactions.

20 Claims, 12 Drawing Sheets

OTHER PUBLICATIONS

Bond CA et al. 2006. Adverse drug reactions in United States hospitals. Pharmacotherapy 26:601-08.

Pedro Reinares, L and E Gutierrez De Mesa. 2007. Fostering the process of adoption of personalized medicine: A matter of communication or a matter of cost? Journal of Commercial Biotechnology 13:199-207.

McWilliam A et al. 2006. Health care savings from personalizing medicine using genetic testing: the case of Warfarin. AEI-Brookings Joint Center for Regulatory Studies, Working Paper 6-23, Nov. 2006.

Gurwitz D and HL McLeod, HL. 2007. Primum non nocere. Adverse drug events must be taken seriously: Pharmacogenomics 8:311-314.

* cited by examiner

Fig. 2

START

1. ENTER A PATIENT IDENTIFIER AND CALL UP AN INTERACTIVE WEBPAGE CONTAINING A MEDICAL RECORD RELATING TO THE PATIENT. THE MEDICAL RECORD CAN INCLUDE A PHENOTYPE

2. ENTER A LIST CONTAINING A PLURALITY OF FACTORS ASSOCIATED WITH THE PATIENT IDENTIFIER, WHERE THE FACTORS ARE SELECTED FROM PRESCRIPTION DRUG USAGE(s), SUBSTANCE USAGE(s), CLINICAL FACTOR(s) AND OPTIONALLY, PHENOTYPE(s). IF A GENOTYPE IS ENTERED, THE GENOTYPE WILL BE TRANSLATED INTO A PHENOTYPE

3. ON COMMAND, THE HOST SYSTEM WILL GENERATE AND DISPLAY A TYPE II REPORT BY PERFORMING THE TYPE II PK PREDICTIVE ALGORITHM OF FIG. 5

4. THE SYSTEM WILL FLAG THE OPERATION AS A PHARMACOGENETIC INTERPRETIVE SERVICE FOR AUTOMATED BILLING, AND GENERATE AN INVOICE TO A PAYOR; IN A PREFERRED CASE TO A THIRD PARTY PAYOR.

END

Fig. 3

START

1. THE HOST OPERATOR PROVIDES A HOST SYSTEM (20) HAVING A FIRST GRAPHICAL USER INTERFACE (30) WITH MEANS FOR A CLIENT LABORATORY TO ENTER A PATIENT RECORD INCLUDING PATIENT IDENTIFIER AND A GENETIC TEST RESULT ON BEHALF OF A CUSTOMER OF THE CLIENT LABORATORY

2. HOST SYSTEM RESOURCES ARE THEN USED TO PERFORM THE FOLLOWING OPERATIONS:

A. TRANSLATE GENOTYPE(s) INTO PHENOTYPE(s), IF NOT IN RECORD
    B. USE A TYPE I PREDICTIVE ALGORITHM TO SCREEN A LIST OF DRUGS FOR DRUG-GENE INTERACTIONS; FOR EACH CHANGE % AUC GREATER THAN THRESHOLD VALUE, ADD THE DRUG TO A SUBLIST
    C. GENERATE A TYPE I LAB REPORT, REPORTING A PATIENT IDENTIFIER, LABORATORY IDENTIFIERS, A PHENOTYPIC INTERPRETATION OF THE GENETIC TEST RESULT(s), AND THE SUBLIST OF DRUGS FOR WHICH METABOLISM IS LIKELY TO BE IMPACTED BY THE PHENOTYPE, INCLUDING PREDICTED CHANGE % AUC (UP OR DOWN) RESULTING FROM THE DRUG-GENE INTERACTION, AND A HYPERLINK TO A SECOND GRAPHICAL USER INTERFACE (50) OF THE HOST SYSTEM, (WHEREBY THE CUSTOMER MAY ACCESS THE HOST SYSTEM DIRECTLY) AND DISPLAY THE LAB REPORT

3. SECURELY TRANSMIT THE TYPE I LAB REPORT TO THE CUSTOMER

4. WHEN THE CUSTOMER ACCESSES THE HOST SYSTEM DIRECTLY AT THE SECOND GRAPHICAL USER INTERFACE (50), THE HOST SYSTEM PROVIDES AN INTERACTIVE WEB PAGE THAT RECOGNIZES THE CUSTOMER, DISPLAYS THE PATIENT RECORD AND ALLOWS THE CUSTOMER TO ENTER A LIST CONTAINING A PLURALITY OF FACTORS TO BE ASSOCIATED WITH THE PATIENT RECORD, WHERE THE FACTORS ARE SELECTED FROM PRESCRIPTION DRUG USAGE(s), SUBSTANCE USAGE(s), AND CLINICAL FACTOR(s)

5. THE HOST SYSTEM THEN RUNS A TYPE II PREDICTIVE ALGORITHM (SEE FIGS. 5-7) AND REPORTS A PREDICTION ASSESSING DRUG-DRUG and DRUG-GENE BIOCOMPATIBILITY AMONG THE FACTORS ON THE LIST (ie. A TYPE II REPORT)

6. THE HOST SYSTEM FLAGS THE OPERATION AS A PHARMACOGENETIC INTERPRETIVE SERVICE FOR AUTOMATED BILLING AND OBTAINS REIMBURSEMENT FOR THE DIRECT ACCESS; IN A PREFERRED EMBODIMENT OBTAIN REIMBURSEMENT FROM A THIRD PARTY PAYOR

END

Fig. 4

START

1. THE HOST OPERATOR PROVIDES A HOST SYSTEM (20) HAVING A GRAPHICAL USER INTERFACE (30) WITH MEANS FOR A CLIENT LABORATORY TO ENTER A PATIENT RECORD INCLUDING PATIENT IDENTIFIER, LABORATORY IDENTIFIERS, AND A GENETIC TEST RESULT

2. HOST SYSTEM RESOURCES ARE THEN USED TO PERFORM THE FOLLOWING OPERATIONS:

A. TRANSLATE GENOTYPE(s) INTO PHENOTYPE(s), IF NOT IN RECORD

B. COMPILE A SUBLIST OF SELECTED DRUGS IN DATABASE (22) BASED ON THERAPEUTIC CLASS AND OTHER PARAMETERS AND UNBUNDLE THE LIST

C. SEARCH DATABASE FOR RELEVANT PUBLISHED CLINICAL STUDIES; EXTRACT DATA RELATED TO SELECTED DRUG(s) METABOLISM AND INTERACTION WITH PHENOTYPE(s), AND DETERMINE VALUES FOR INTX AND FRACTION $R_{1/1-n}$ FROM LITERATURE SOURCES

D. IF PATIENT PHENOTYPE ABNORMAL, USE A PREDICTIVE ALGORITHM TO CALCULATE CP FOR EACH DRUG ON SUBLIST

E. CALCULATE $\Sigma$CP FOR EACH DRUG, SUMMING EFFECTS OF MULTIPLE PHENOTYPES IF ANY F. CONVERT $\Sigma$CP TO CHANGE % AUC (UP OR DOWN) VALUES (SEE FIG. 8)

G. IF CHANGE IN CP IS LESS THAN A THRESHOLD LEVEL AND NO CLINICAL WARNINGS, DELETE DRUG FROM SUBLIST

H. GENERATE A TYPE I LAB REPORT, REPORTING A PATIENT IDENTIFIER, LABORATORY IDENTIFIERS, A PHENOTYPIC INTERPRETATION OF THE GENETIC TEST RESULT(s), AND A TABULATED SUBLIST OF DRUGS FOR WHICH METABOLISM IS LIKELY TO BE IMPACTED BY THE PHENOTYPE, INCLUDING PREDICTED CHANGE % AUC (UP OR DOWN) RESULTING FROM THE DRUG-GENE INTERACTION, AND DISPLAY THE LAB REPORT

3. THE CLIENT LABORATORY OR HOST SYSTEM WILL THEN FLAG THE REPORT AS A PHARMACOGENETIC INTERPRETIVE SERVICE FOR AUTOMATED BILLING

4. IN A PREFERRED EMBODIMENT, THE CLIENT LABORATORY WILL THEN BILL A THIRD PARTY PAYOR (OR END USER) FOR THE SERVICE AND WILL REMUNERATE THE HOST SYSTEM OPERATOR FOR THE COST OF ACCESS TO THE HOST SYSTEM

END

Fig. 5

START

1. ENTER ALL FACTORS, INCLUDING DRUGS, BIOACTIVES, PATIENT CHARACTERISTICS, AND GENOTYPE(s) INTO A LIST THROUGH GUI 50

2. UNBUNDLE THE FACTORS, IDENTIFYING COMPONENTS OF MIXTURES, PRODRUGS, ENANTIOMERS, METABOLITES AND CLASS MEMBERSHIPS

3. TRANSLATE GENOTYPE(s) INTO PHENOTYPE(s), IF NOT DONE SO

4. IDENTIFY INHIBITOR AND INDUCER FACTORS

5. IDENTIFY POTENTIAL VICTIM SUBSTRATES AND METABOLIC PATHWAY(s) FOR POTENTIAL VICTIM(s)

6. FOR ALL METABOLIC PATHWAYS INVOLVED IN THE METABOLISM OF ANY VICTIM SUBSTRATE, FIND ALL POTENTIAL INTERACTION PAIRS, AND IDENTIFY THE CULPRIT (INHIBITOR OR INDUCER) IN EACH

7. FOR EACH VICTIM SUBSTRATE FROM STEP 6, CALCULATE A CP SCORE:

$$CP = INTX * (FRACTION\ R_{1/1 \to n})\quad \text{[SEE SUBROUTINE A]}$$

8. FOR EACH VICTIM SUBSTRATE, CALCULATE $\Sigma CP$ BY SUMMING ALL CPs FOR THE VICTIM.

$$\Sigma CP = (CP_{[Route\ 1]} + CP_{[Route\ 2]} + \ldots CP_{[Route\ n]})$$

9. FOR EACH VICTIM, CALCULATE A PREDICTED CHANGE % AUC (SEE FIG. 8)

10. FOR EACH POTENTIAL INTERACTION PAIR, SEARCH DATABASE FOR ANY RELEVANT PUBLISHED CLINICAL STUDY; EXTRACT WARNINGS AND NOTES AND INTEGRATE THE WARNINGS AND NOTES, IF ANY, WITH THE PREDICTION OF STEP 9.

[SEE SUBROUTINE B]

11. BUILD A WEBPAGE DISPLAYING SUMMARY OF CALCULATED PREDICTION(s) AND CLINICAL EXPERIENCE

END

Fig. 6
SUBROUTINE A

TO CALCULATE A CP SCORE FOR THE VICTIM IN EACH INTERACTION PAIR,

1. LOOK UP INTX — THE INTENSITY INDEX FOR INDUCTION OR INHIBITION OF THE PATHWAY BY THE CULPRIT

2. CALCULATE FRACTION $R_{1/1-n}$ BY DIVIDING THE NOMINAL METABOLIC CLEARANCE VIA THE AFFECTED PATHWAY BY THE TOTAL METABOLIC CLEARANCE THROUGH ALL PARALLEL PATHWAYS

3. MULTIPLY INTX BY FRACTION $R_{1/1-n}$ $$CP = INTX * (FRACTION\ R_{1/1-n})$$

| Points (81) | Patient's Exposure to drug (82) | "Change" Reported in Output Column 2 (83) | Change in drug level (%) (84) |
|---|---|---|---|
| -100 | Almost no exposure | -3 | 90-100 |
| -50 | Substantial decrease | -2 | 60-90 |
| -25 | Modest decrease | -1 | 25-60 |
| 0 | Minimal | 0 | <25 |
| +25 | Modest increase | +1 | 25-75 |
| +50 | Substantial increase | +2 | 75-150 |
| +100 | Extreme increase | +3 | >150 |

SUBROUTINE B

1. CREATE A PRIORITIZED LIST (HIGHEST FIRST) AS FOLLOWS:

A. ANY WARNING OF A POTENTIAL MAJOR ADVERSE INTERACTION BETWEEN THE INTERACTING PAIR REPORTED IN A PUBLISHED CLINICAL STUDY

B. ANY LESSER CHANGE NOTED IN A CLINICAL STUDY

C. ANY MAJOR CHANGE WARNING PREDICTED BY THE PK PREDICTIVE ALGORITHM (FIG. 5, STEP 10)

D. ANY LESSER CHANGE PREDICTED BY THE PK PREDICTIVE ALGORITHM

2. REPORT A PREDICTION OF CHANGE IN VICTIM METABOLISM BASED ON THE HIGHEST PRIORITY ENTRY FROM THE LIST ABOVE

3. SEARCH DATABASE FOR ANY NOTES ASSOCIATED WITH THE REPORT AND DISPLAY THEM

Fig. 9

| GeneMedR$_\times$ | Sample Lab Report - Type I          171 |
|---|---|
| | DRUG DNA REACTION TEST RESULTS |
| | Cytochrome P450 2D6                   173 |

Patient: John Doe     Phenotype:    Poor Metabolizer     11/16/2007
Genelex Lab #50-574    Genotype:     CYP2D6*3/*4
Sample Collected 11/10/2007            Laboratory Director: ML~~~~~~~~, PhD

Additional Interpretive Report. A personalized drug and gene interaction report based on individual patient medication regimes can be created by accessing your patient record at www.GeneMedRx.com/login/. You will need the following information to log in: Account Access: User Name: John Doe, DOB: 11/18/50, Password: Apo*IdaZRxL.

Laboratory Test Interpretive Comments: DNA testing has determined that the tested individual is a CYP2D6 Poor Metabolizer. As a result CYP2F6 enzyme activity is greatly reduced or completely absent in this individual. Elimination or activation of approximately one-quarter of commonly prescribed medicines, including over-the-counter and herbal preparations, requires CYP2D6 enzyme activity. The majority of affected medicines require CYP2D6 activity for deactivation. At the standard dose, individuals who are 2D6 Poor Metabolizers will have increased exposure to substances dependent on CYP2D6 for their elimination. This may or may not lead to adverse drug reactions similar to those caused by overdose. Patient monitoring for adverse effects is advised and dose adjustments may be considered. Some medicines are prodrugs and require CYP2D6 activity for conversion to the active form. At the standard dose this may result in lack of efficacy as well as increased toxicity.

Analytical Comments – Cytochrome P450 2D6 alleles tested.
Active alleles: CYP2D6 *1 or *2
Partially active alleles: *9 or *10 or *17
Inactive alleles: CYP2D6 *3 or *4 or *5(deletion) or *6 or *7 or *8 or *11 or *12
Gene Duplication: *1 or *2 or *4 or *10

Analytical specificity and sensitivity for detection of these mutations are >99%. Other known variants not listed are not detected. Laboratory specimens were analyzed using the Tag-It™ Mutation Detection System.

Gene Drug Interaction Tables. These tables have been prepared from the most recent update of the GeneMedRx drug interaction database to assist in interpretation of the cytochrome P450 DNA test results. The tables provide an estimate of the change in overall patient exposure to the listed substances based on the reported genotype. They do not take into account drug interactions. More detailed information and complete references are available at www.GeneMedRx.com or in the glossary below.

| Drug | Percent Change in patient exposure to active form | Drug | Percent Change in patient exposure to active form |
|---|---|---|---|
| Cancer | | | |
| Gefitinib = Iressa | ⬆ +less than 25% | lomustine = CeeNu | ⬆ +more than 150% |
| idarubicin = Idamycin | ⬆ +75 to 150% | | |
| Cardiovascular | | | |
| ajmaline | ⬆ +more than 150% | minapril | ⬆ +more than 150% |
| captopril = Capten | | | |

Fig. 13

GeneMed

| CURRENT TASK: SELECK A PAYMENT OPTION |
|---|

From here you can get many kinds of access including plans for pre-registered users and students.

Which Applies to You?

212 — ○ I am a medical professional or administrator
● I will be using GeneMedRx for myself or my family

Medical Professionals and Administrators

211 —
○ Free Trial Subscription
○ Buy or extend a subscription (including affiliated groups)
○ Activate a subscription included with DNA testing — 213
○ Student subscription (See eligible student groups.)

NEXT →
Enter = Next

210

GENETIC DATA ANALYSIS AND DATABASE TOOLS

CROSS-REFERENCE TO RELATED APPLICATIONS

This application claims priority to provisional patent application Ser. No. 60/901,528 and to provisional patent application Ser. No. 61/026,724, from which priority is claimed under 35 USC 119(e).

BACKGROUND

Traditionally, physicians have been expected to retain in memory knowledge relating to potential adverse drug reactions, pharmacology, and pharmacogenetics, or to have access to such information from published (generally hard-copy) reports—information that is not accessible from a single source and which is increasingly complex. More recently, some classes of information, for example labeling warnings published in the PDR, have become accessible through wireless and PDA devices. There is increasing interest in expanding the availability of this kind of information at the point of care.

A basic problem with all such information, however, is the need for computer systems, databases, networks, and software tools to display and bring to the foreground the information most relevant to the issue at hand, a problem that requires extensive software development. In short, it is no longer sufficient to merely publish information in the form of a text book or a reference manual. But because of the difficulty in obtaining reimbursement for the costs of the software services and databases, progress toward sustainable software innovation and deployment has been disappointing. Thus, there is a need in the medical arts for business models to support computerized implementation of systems designed to store and process metabolic, pharmacologic, and pharmacogenetic data (herein "metabolomic data"), to interpret that data in the context of patient-specific factors such as age, pregnancy, smoking and use of alcohol (herein "clinical factors", or "patient characteristics"), to make available that data at the point of care, prioritized by relevance, and to provide integrated reimbursement tools for the costs of the equipment, database updates and maintenance. Needed are business models that support implementations of these computerized tools.

Mental Health Connections (Lexington, Mass.) was an early entrant into computerized medical bioinformatics services. Their GeneMedRx service, introduced in 1995, was initially based on computerized tables for looking up drug interactions as a function of induction or inhibition of the cytochrome P450s involved in their metabolism. In 2006, in partnership with Genelex (Seattle Wash.) testing was begun on systems for interpretation of drug-drug and drug-gene interactions within the framework of a patient's overall medication regimen. In recent versions, GeneMedRx has grown as a database and now recognizes transporter and conjugation-linked as well as cytochrome P450-linked drug interactions. The drug interaction service now also includes a novel predictive algorithm. These efforts have provided valuable lessons in the need for improved business models to successfully commercialize various aspects of bioinformatics.

Marchand (USPA 2006/0289019) describes computer systems for optimizing medical treatment based on pharmacogenetic testing and Pareto modelling. But the disclosure is silent as to how to pay for these systems. Pickar (USPA 2003/0104453) describes computer systems for minimizing adverse drug events but is silent with respect to means to recover the costs. Hoffman (USPA 2004/0197813 and USPA 2004/0199333) describes a method for determining whether an atypical response to drug therapy is attributable to an error in metabolism but again does not describe a business method. Early work describing the application of computers to pharmacogenetics is described in a 1999 paper by Evans and Relling (Science 286:487-491), a 2000 paper by Ichikawa (Internal Medicine 39:523-24), and in a patent application that same year by Reinhoff (US 2002/0049772). Reinhoff describes a computer implementation of a program on a networked computer for analyzing polymorphisms in human populations and using this information to, for example, "gauge drug responses", but these citations again do not address reimbursement concerns.

Although Gill-Garrison in U.S. Pat. No. 7,054,758 describes computer preparation and delivery of genetic reports that include "personalized dietary advice", the report service as commercialized (Sciona, Boulder Colo.) is limited to direct marketing to consumers by the testing laboratory under 'fee-for-service' arrangements and does not contemplate methods for billing such as 'pass-through' reimbursement models or wholesale services to contract laboratories or clinics. Nor does the service quantitate or extrapolate the effects of impacting substances or factors (as practiced and defined here) on the pharmacokinetics of drug metabolism, for preparation of reports relying instead on a simple look-up table or tables to correlate "advice" with "risk factor" and genetic polymorphism.

Holden (USPA 2004/0088191) addresses the issue of secure access to genetic test results over a network and the use of passwords to share genetic test data with third parties such as physicians. Dodds (USPA 2003/0135096) again recognizes the security issues, but sees that secure access can be linked to payment authorization in a simple fee-for-service model with on-line authorization of credit card purchases. Issued U.S. Pat. No. 7,054,755 also proposes prior art financial service means, specifically means to purchase genetic testing kits electronically, in what is basically a shopping cart model such as might have been assembled from the teachings of U.S. Pat. No. 5,960,411, the "one-click" patent to Amazon.com, and related arts.

However, an invitation to the customer to pay directly for preventative medical care, for example genetic testing, has not been generally appealing or successful. More typically, customers will habitually defer the costs of preventative medicine. Thus, whereas Larder in U.S. Pat. No. 7,058,616 states, "The main challenge in genotyping is the interpretation of the results" (Col 9, lines 27-28), to the contrary we have found that the main challenge is supporting the costs of the required servers, databases, networks and programming. A particularly preferred model, as disclosed here, eliminates the need for mental processes in operation of the system. Genetic testing services are thus still in need of improved business models built on automated systems, business models capable of generating sufficient revenue to support their development and implementation at the point of care.

SUMMARY

Significant efficiencies in patient care are anticipated from computerization of medical and genetic data related to drug metabolism, herein "metabolomics". Metabolomics includes not only drug-drug and drug-allele interactions, but drug interactions precipitated by foods, over-the-counter medicines, herbal preparations, or clinical factors such as age, pregnancy, smoking, alcohol use, liver disease, and so forth.

As an example of potential medical benefits and cost savings, consider the potential savings and reduced mortality and morbidity by preventing adverse drug reactions (ADRs) to prescribed drugs. According to the FDA, it is estimated that "there are more than 2,216,000 serious ADRs in hospitalized patients, causing over 106,000 deaths annually. If true, then ADRs are the 4th leading cause of death—ahead of pulmonary disease, diabetes, AIDS, pneumonia, accidents, and automobile deaths." In another study, "The total cost for patients with an ADR increased an average of $2401/patient (19.86% increase), . . . . Extrapolating this finding to the entire Medicare population resulted in $516,034,829 in costs associated with ADRs" (Bond C A et al. 2006. Adverse Drug Reactions in United States Hospitals. Pharmacotherapy 26:601-608). Also to be considered are the cost of treatment failures resulting from ADRs.

ADRs have many causes, and one of the most important and hardest to predict, but also most preventable cause, is interactions between drugs, herbals, foods (generally, "substances") and individual genotype. Another important class of these interactions are drug-drug interactions (DDIs).

In our invention, predictive algorithms are provided that can prevent many ADRs by issuing warnings on a graphical user interface at the point of care before the prescription is written. Graphical user interfaces for querying hierarchical databases are gateways for transforming raw data into customized reports or "views" relevant in real time to weighing the risks and benefits of therapeutic options. Each graphical user interface (GUI) also serves as a "paypoint" for automated management of reimbursement.

The novel PK predictive algorithms disclosed here have been found to be surprisingly effective in predicting drug interactions of the types associated with ADRs, and hence contributes to their prevention. Our PK predictive algorithms provide a way to make quantitative predictions of metabolism-based interactions among substances for which there are metabolic data but not clinical studies. The absence of clinical studies is a serious issue; as there are thousands of drugs and other substances the paired interaction of which have not been studied. Rarely, clinical studies report on simultaneous interactions among multiple substances. Far more data is available on the metabolism of drugs and substances, mostly in the form of pharmacokinetic (PK) data, and it is this information that is used to make drug interaction predictions by the algorithms of the present invention.

The algorithms can also runs a comparative subroutine, in which known clinical studies of drug and substance interactions are tabulated so that the quantitative predictions of the algorithm can be compared against published results, thus validating the performance of the algorithms. The supporting databases are frequently updated to extend the scope and power of the PK predictive algorithms.

One such PK predictive algorithm described here is a multifactorial algorithm capable of predicting drug-drug, drug-substance, drug-gene, substance-gene, drug-clinical factor, substance-clinical factor, and multiple complex interactions, many of which have been associated with adverse drug interactions. While in the text there are frequent references to 'drug-drug' and 'drug-gene' interactions, these should be interpreted broadly to include drug-factor, substance-factor, gene-factor, and clinical factor-factor (or "patient characteristic"-factor) interactions. The predictive algorithms have been shown to be capable of processing superimposed interactions among multiple factors.

Tools and methods for production, processing and delivery of metabolomic and pharmacogenetic interpretive information are also disclosed, comprising a digital, computer-implemented system having algorithms and databases for storing, collating, accessing, cross-referencing, and interpreting genetic and pharmacologic data, and a network or networks whereby contracting client laboratory providers of genetic testing services, and other customers, can access the core host servers. The Host System includes interactive software engines (the "Medical Metabolomics Engine" and the "Lab Report Engine") that support an improved business model for genetic testing, test interpretation, test reporting, and assist in prevention of ADRs.

The Host System is configured for preparation of two kinds of reports: The first report type (Type I) is used by laboratories (with access to the Host System under contract) to report genetic test data to their customers. It provides a formatted test report containing patient's genotype, diagnosis of the resulting phenotype, and drug-gene interaction information—detailed lists of drugs for which drug metabolism is impacted by the phenotype, for example. It is generated by the Host System's Lab Report Engine, but optionally may be formatted with the logo and look of the reporting contract laboratory. The second report type (Type II) is generated, for example, when the patient or an authorized user of report Type I logs onto the central platform directly and enters added confidential medical information such as drugs currently taken, herbal usage, certain foods in the diet, and clinical or "patient characteristic" factors such as smoking or pregnancy. The Host System includes highly interactive GUIs with tools to select and display views of the most contextually relevant analysis of drug-drug and drug-gene metabolic interactions based on patient-specific information inputted by the user, who may be the patient or a health care provider. The Type II report is generated on the fly in response to the patient entries, and is a fully interactive webpage with multilevel displays, including for example: ranked warnings on possible drug or herbal interactions specific to the patient's drug regime or proposed prescription use, suggestions for alternative drugs in the same therapeutic class, annotations with links to the medical literature, recommendations for added genetic testing, and so forth.

Both the Type I and Type II interaction reports thus use a PK predictive algorithm. The Type I report includes a drug-gene interaction report for drugs selected by the host system. The Type II report can include drug-drug interaction reports, where the drugs are selected by the user based on current medications. The Type II report is thus a personalized tool for use in managing medications. The predictive algorithms used in the two report types are thus modified for the purpose to which they are employed, and can be modified further for use with other interacting factors.

The two report types are presented on different GUIs. In the current embodiment, the Type I report is presented by either of two GUIs built into the Lab Report Engine. The Type II report is presented by a GUI specific for the Medical Metabolomics Engine, as will be explained further.

Both Type I and Type II report interfaces are accessible in real time on any network, including the world wide web, including wireless telephones and PDAs, or on an intranet or wireless intranet network. "Informational transaction" or "data exchange" events can be captured for billing purposes as by credit card, subscription, direct billing, online debiting, or third party billing. In this way, a long-sought need is at last met for a system that provides flexible billing tools in support of covering the costs of the information technology support required for widespread genetic testing and use of pharmacogenetic interpretive services.

There are differences in how the two report types are reimbursed. The Type I report, containing a genetic test result and diagnosis of a phenotype, is typically generated by the Host System at the request of an outside laboratory accessing the Lab Report Engine under subscription or contract, and can be billed by the laboratory to a third party payer such as an insurance company under "current procedural terminology (CPT codes) codes", or other reimbursement codes, from which the costs of maintaining and updating the core servers and databases can be paid to the Host System operator. These fees can also be paid by credit card directly by the patient receiving the report but this has been shown not to be a preferred method. Automated fees for the Type II report are established for different market segments, including free trial access, monthly or yearly subscription access, "pay-per-ping" access, wholesale access, and in a preferred embodiment, third party 'pass through' billing by use of the appropriate reimbursement codes (such as when the service is used by physicians during office visits), and so forth. Use of pass through billing, which frees the patient from the cost of the service, also frees the physician or health care provider to make greater use of the service.

The Type I report is automatically updated by the predictive algorithm each time it is accessed on-line. In an improved reimbursement model, the Type I report contains interactive links and security access codes so that the recipient can access the Type II report service, thus enabling the Host Operator to convert client laboratory customers to direct-service customers.

A "sponsored-use hyperlink" embedded in a Type I report in the above method has the property that when securely accessed by entering the patient's identifiers and access code from a remote terminal, such as at a doctor's office or a home, a Type II report is created that includes updated metabolomic content from Host System databases and offers a series of interactive options. The Type II report is presented by a GUI dedicated for this purpose. Here, the patient may enter personal information such as current prescription drug usage, relevant clinical factors such as pregnancy, age, history of smoking, and so forth. Displayed in the resulting Type II report are detailed DDI ("drug-drug interaction") and ADR warnings specific to the patient's personal drug regime and personal genetic data at that moment in time. In other words, the Type II report, given a phenotype and a personal drug regimen, can predict both drug-drug and drug-gene interactions of possible immediate concern to the user. A user may modify the drug regimen to remove the culprit drug or drugs responsible for the warning and generate an updated report. In this way it is possible to check a prescription for potential DDIs or ADRs before it is written. This report is updated on the fly whenever the patient, or anyone the patient authorizes to access the records (e.g. a physician) accesses the Host System if the core databases have been updated with relevant new clinical information or if there is a change in the patient's medical regimen or status. The services provided by this GUI are billable in several ways: as a "pay-per-ping" fee to the patient or to the physician, as a subscription service to the patient or to the physician, as a free trial, wholesale to a clinic, or to third parties through the mechanism of a CPT code or other reimbursement code arranged for third party billing, and so forth. This innovative service also will function in a single-payor insurance model.

Whereas the initial laboratory report (Type I) can be billed by the client laboratory to the end use customer (e.g. patient or physician) or to insurance, the second report (Type II) is configured as a direct transaction with the Host Server, and thus results in fees directly payable by the customer to the operator of the Host System. By including in the Type I report a link to the Type II user interface, the first report thus generates what is essentially a business referral to the Host System. This is beneficial to all parties because it allows the patient or health care provider to better manage ADRs, and encourages use of genetic testing. The Type II user interface may also display recommendations for further genetic testing services if indicated, or links to related services such as paternity testing services, and thus becomes a central hub in a network for accessing a broad range of medical and genetic services or information.

BRIEF DESCRIPTION OF THE DRAWINGS

The teachings of the present invention can be readily understood by considering the following detailed description in conjunction with the accompanying drawings, in which:

FIG. 2 is a flow diagram illustrating the operation of Paypoint 1.

FIG. 3 is a flow diagram illustrating the operation of Paypoint 2.

FIG. 4 is a flow diagram illustrating the operation of Paypoints 3, 4 and 5.

FIG. 5 is a flow diagram outlining the major steps of a PK predictive algorithm and showing subroutines A and B.

FIG. 6 is a detail showing the steps of subroutine A.

FIG. 7 is a detail showing the steps of subroutine B.

FIG. 8 is an example of a table used by a computer algorithm for making calculations of the effect of interacting factors on the AUC of a drug.

FIG. 9 is an example of an experimental Type I lab report containing a "sponsored-user" hyperlink.

FIG. 13 is a detail of an interactive screen demonstrating a computerized tool for use of market segmentation in a business plan for vending genetic information and interpretation services.

DETAILED DESCRIPTION

Figure 1:
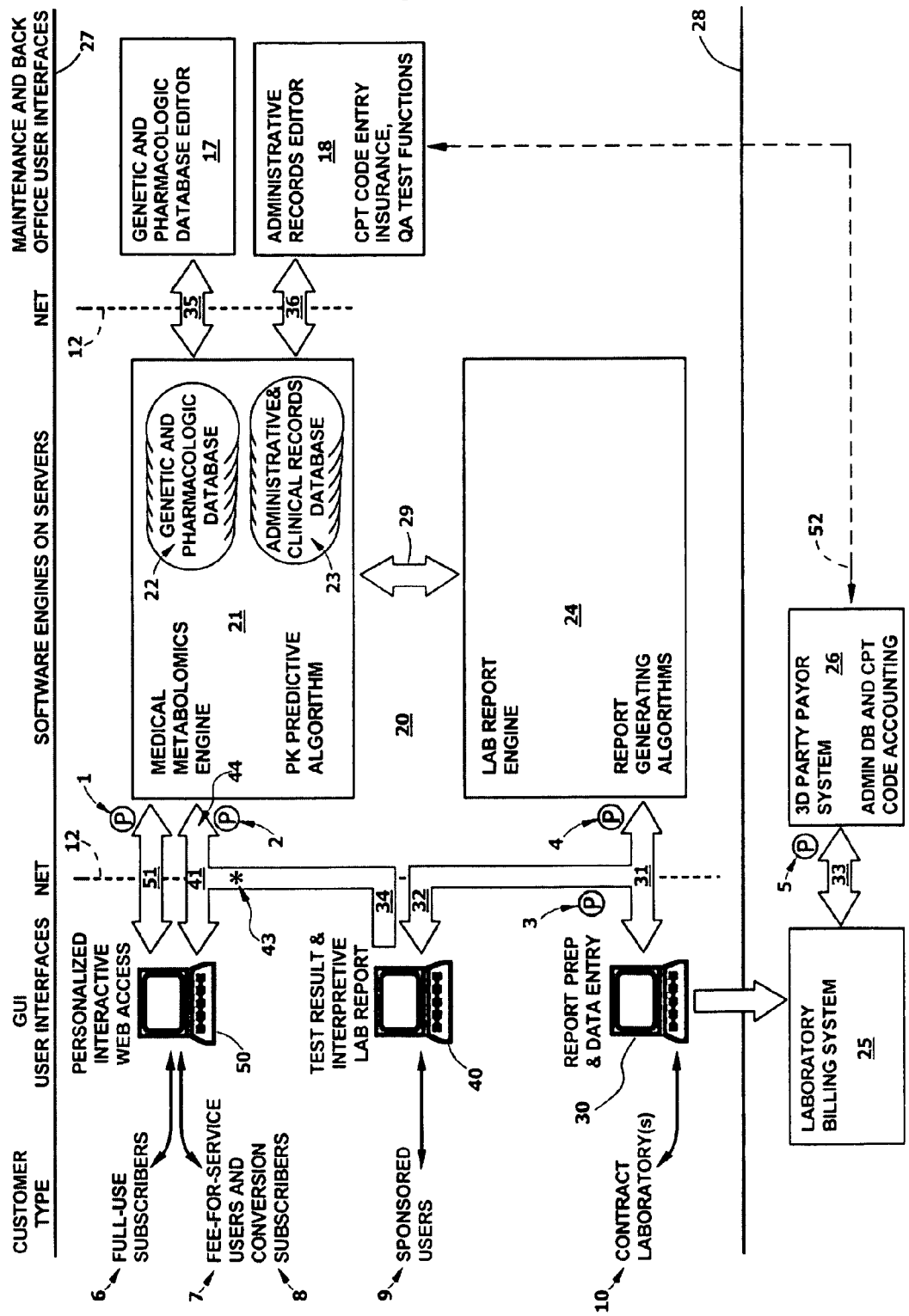
FIG. 1 is a schematic of a computerized apparatus for storing, collating, accessing, crossreferencing and interpreting metabolomic data, with multiple GUIs capable of supporting a segmented business model.

Although the following detailed description contains specific details for the purposes of illustration, one of ordinary skill in the art will appreciate that many variations and alterations to the following details are within the scope of the invention as claimed. Accordingly, the exemplary embodiments of the invention described below are set forth without any loss of generality to, and without imposing limitations upon, the claimed invention.

Adverse Drug Reaction (ADR): as used here, describes a response to a drug or substance which is noxious and unintended, and which occurs at doses normally used in man for prophylaxis, diagnosis, or therapy of disease, or for modification of a physiological function. ADRs have many causes and one the most important and hardest for clinicians to predict, but often most preventable cause, is interactions among drugs, herbals, foods and genetic factors. At the molecular level, a comprehensive treatment includes both Phase 1 and Phase 2 metabolic systems, including conjugation enzymes (such as uridine diphosphglucuronylsyltransferases and sulfotransferases), transporters (such as ABC and SLCO), as well as the known cytochrome P450 oxidative enzymes.

Phase I reactions can occur by oxidation, reduction, hydrolysis, cyclization, and decyclization reactions. Oxidation involves the enzymatic addition of oxygen or removal of hydrogen, carried out by mixed function oxidases, often in the liver. These oxidative reactions typically involve a cytochrome P450 haemoprotein, NADPH and oxygen. If the metabolites of phase I reactions are sufficiently polar, they may be readily excreted at this point. However, many phase I products are not eliminated rapidly and undergo a subsequent "Phase II" reaction in which an endogenous substrate combines with the newly incorporated functional group to form a highly polar conjugate.

Phase II reactions (e.g., glucuronidation, sulfonation, glutathionyl-conjugation or amino acid conjugation) speed clearance by increasing polarity, and involve conjugation at functional groups formed in Phase I metabolism.

Information about genetic loci responsible for polymorphisms of Phase I and Phase II enzymes and associated transporters is thus of significance in making predictions about potential ADRs. Drug-drug; substance-substance; drug-gene; substance-gene, and more generally "substance-factor" interactions must be considered in assessing possible ADRs.

Drug-Drug Interactions (DDI): include interactions between pairs of drugs or substances and among multiple drugs or substances that result in changes in the pharmacokinetic parameters of one of the interacting drugs or substances. Drug-drug interactions (DDIs) are not ADRs but many ADRs are caused by DDIs. We note that some drug interactions are beneficial because the inhibition of metabolism of a drug can increase the patient's exposure to it and increases the therapeutic benefit. Among such interactions, the cytochrome P450 system, which plays a major role in metabolizing drugs and other potentially toxic substances, is believed responsible for about 70% of DDIs.

Drug: is a substance used as a medicine.

Prodrug: is a drug which is not therapeutically active until it undergoes metabolism in the body.

Bioactive: a substance with biological activity. Bioactive is a broad term encompassing drugs, foods, herbals, and so forth. More specific examples not named elsewhere include lipids, surfactants, retinoids and flavonoids. Also included are metabolites of foodstuffs, drugs and substances.

Food: a substance ingested for flavor or nutrition.

Herbal: a plant or plant derived substance used for its therapeutic properties.

Substance: a drug, bioactive, excipient, herbal, food, or other chemical. As used herein, a drug-drug interaction can refer to a substance-substance interaction. More generally, a substance-factor interaction refers to a substance-substance, substance-gene, or substance-clinical factor interaction.

Factor: includes substances, bioactives, phenotypes, and "patient characteristics", also termed "clinical factors", which may cause or be subject to an interaction. Importantly, in the algorithms, factors are specific to and associated with a patient identifier. Drug class membership (below) is also a factor.

"Clinical factor" or "patient characteristic": as used here, includes any patient-specific characteristic, classification or status, such as pregnancy, age, race, history of smoking or alcohol use, liver pathology, kidney pathology, cholecystectomy, colostomy, diabetes, lifestyle, and so forth, that can cause or exacerbate a substance interaction, DDI, or ADR. Clinical factors are generally drawn from the clinical history. The list of factors is expansible within the table structure of a database and can be used in an algorithm to predict potential DDIs and ADRs, as taught here.

Drug "class membership": as used here is also a "factor" in the context of the PK predictive algorithm and is directed to a "synthetic" class or group comprised of drugs with a common side effect. Many SSRI's for example share common side effects. Certain other drugs commonly cause QT/QTc prolongation, slowing the heart rate, such as risperidone and haloperidol. Simultaneous administration of two such drugs can lead to additive side effects, a DDI that is not directly linked to a genetic polymorphism (although it would be exacerbated by one), but is picked up and displayed by the Type II PK predictive algorithm.

"Medical metabolomics", or "metabolomics" as used here, includes elements of pharmacogenetics, pharmacology, naturopathy, biochemistry, physiology and medicine. We limit the scope of the information, strictly for the sake of relevance, to the patterns of metabolism of drugs and other bioactives jointly "substances") and their interaction with metabolic enzymes and transporters and with each other in the complex environment of the human body. Of particular interest is the question of the effect of these interactions on the pharmacokinetics, efficacy and safety of a particular drug in a particular patient. Thus metabolomics includes the study of ADRs.

Bioinformatics: Bioinformatics derives knowledge from computer analysis of biological data. These data can consist of the information stored in the genetic code, but also include experimental results from various sources, patient statistics, and scientific literature. Research in bioinformatics methods and apparatuses is ongoing, and includes algorithm development for storage, retrieval, and analysis of the data.

Pharmacogenetics: Refers to the evaluation of individual genetic variation in relation to the delivery, safety, and effectiveness of drugs. Knowledge of individual genotypes and phenotypes makes it possible to customize drug delivery regimens for specific patients so as to avoid ADRs and maximize the benefits of drug therapies. Additionally, pharmacogenetics encompasses the study of the differences among individuals with respect to gene-linked responses to a drug. Relevant laboratory workups include "genotyping" or "genetic testing" by methods such as array hybridization, PCR-direct sequencing, PCR-linked electrophoretic restriction fragment polymorphism, or PCR-linked allele specific primer extension. Samples include buccal swabs and blood collected by venipuncture or lancet. Genetic markers of interest in pharmacogenetics include polymorphisms at selected allelic loci, particularly SNPs and deletions, often referred to in the literature as "haplotypes" or "star data". More recently, through direct sequencing of whole human genomes, unpaired chromosomal fragments (ie. unpaired alleles) have been discovered in which an individual is mono-allelic, and these too may also have a bearing on health and disease. Relevant pharmacogenetic information includes the testing data, sample and testing protocols, and annotations of the primers or sequence data used for identification of a genotype from, all generally recognized as necessary components of a genetic testing report. Interpretation of pharmacogenetic data commonly requires categorization of the genotype into one or several phenotype classifications, for example slow or poor metabolizer, intermediate metabolizer, normal, and ultra-fast metabolizing forms, as well as various classifications based on the organ in which the gene is expressed.

AUC: also termed "area under the curve", is a measure of the amount of a drug or substance the body is exposed to. It reflects both the time-course and concentration of a drug or substance in bodily fluids.

Inhibitor: generally a ligand interacting with an enzyme, transport, conjugation, allosteric or other binding site and resulting in reduced throughput of the substrate. Inhibition at the level of gene expression is also contemplated by this term. In the PK prediction algorithm, published Ki values are used to estimate the interaction intensity index IP. When a Ki is unknown, a default value is assigned. If the impacting factor responsible for reduced throughput is a phenotype or clinical factor, an index value is assigned based on intensity ratings extracted from the research literature.

Inducer: generally a ligand causing increased expression of a gene responsible for synthesis of an enzyme or transporter. Inducer-specific experimental and clinical ratings of induction intensity are assigned an index value INTX comparable to the points assigned for inhibition but of negative sign. The intensity of inducer effects can be estimated, for example, by Neil's rules of thumb. If the impacting factor responsible for increased throughput is a phenotype or clinical factor, an index value is assigned based on intensity ratings in the research literature.

Interaction pair: refers to substances or factors that interact by increasing or decreasing the metabolism of one member of the pair via one or more metabolic pathways. One of the members of the pair is a substrate of the pathway or pathways and is called the "victim", the other substance or factor is called the "culprit" and can be i) an inducer, ii) an inhibitor, iii) a genetic polymorphism of a gene encoding a protein of the pathway, or iv) other clinical factor such as pregnancy or age. Inducers and inhibitors are not limited to prescription drugs, but may include clinical factors such as exposure to tobacco smoke or environmental chemicals. While victims and substrates interact via metabolic routes, it should be understood that the interaction may involve oxidative enzymes, conjugative enzymes, or transporters, of which cytochrome P450, glucuronyl transferase, and P-glycoprotein are illustrative examples, and that metabolism may be influenced by factors such as age and pregnancy, as well as genetic polymorphism, allosteric and competitive inhibition, and induction of gene expression. Thus "interaction pair" is not limited to drug-drug interaction.

"Victim": is a term of art referring to a member of a drug interaction pair for which metabolic throughput is impacted, resulting in a change in AUC, ie. a change in peak or cumulative exposure.

"Culprit": is a term of art referring to a member of a drug-drug or drug-factor interaction pair responsible for a change in AUC, ie. in peak or cumulative exposure, of a "victim". Because clinical factors can also impact drug exposure, the term "culprit" is used in a broad sense, conveying a list not only of drugs and substances, but also of clinical factors and patient characteristics that can impact a victim drug or substance. Culprits may be inhibitors or inducers.

Intensity: refers to the degree of interaction between two substances or factors. In subroutine A of the PK predictive algorithm, the intensity of interaction is quantitated by "INTX". Intensity indices are drawn from literature values and include indices of induction and inhibition.

Proportion: refers to the relative fraction $R_{1/1-n}$ of a drug or substance's metabolism directed through a particular metabolic pathway where more than one pathway operates in parallel.

Paypoint: an automated tool for flagging, configuring and routing information about a data exchange between the Host System and a user, and initiating an automated financial transaction on a billing server that generates a debit on an account.

Graphical user interface (GUI): a combination of one or more visual, acoustic and tactile means for engaging a computer, commonly based on a mixture of graphics and text that is used to query a database. GUIs include tools such as keyboards and mouse pointers for entering information in a computer.

Genotype: As used here refers to a genetic marker or "allele"—one of several possible hereditable DNA sequences characterizing one genetic locus of an individual. It pertains to a specific gene, but "genotype" may also be used to describe a collection of genotypes for each of a set of genes of an individual.

Phenotype: By contrast, phenotype refers to the manifestation of expressed genetic information, and thus indicates not only a particular protein or set of proteins of an organism or tissue, but also variants in the way protein expression or activity responds to environmental factors.

The following are representative genetic testing data. These include genetic loci that are known to be important in drug metabolism. Also relevant are the disclosures of U.S. Pat. No. 7,054,758, assigned to Sciona Ltd, and US Patent Application 2006/0289019, assigned to IPPM Holding SA, hereby incorporated in full by reference. Also relevant are the disclosures of Tomalik-Scharte (Tomalik-Sharte, D et al. 2008, The clinical role of genetic polymorphisms in drug-metabolizing enzymes. Pharmacogenetics J 8:4-15), hereby incorporated in full by reference.

CYP2D6 (cytochrome P450 2D6) is the best studied of the DMEs and acts on one-fourth of all prescription drugs, including the selective serotonin reuptake inhibitors (SSRI), tricylic antidepressants (TCA), betablockers such as Inderal and the Type 1A antiarrhythmics. Approximately 10% of the population has a slow acting form of this enzyme and 7% a super-fast acting form. Thirty-five percent are carriers of a non-functional 2D6 allele, especially elevating the risk of ADRs when these individuals are taking multiple drugs. Drugs that CYP2D6 metabolizes include Prozac, Zoloft, Paxil, Effexor, hydrocodone, amitriptyline, Claritin, cyclobenzaprine, Haldol, metoprolol, Rythmol, Tagamet, tamoxifen, and the over-the-counter diphenylhydramine drugs, Allegra, Dytuss, and Tusstat. CYP2D6 is responsible for activating the pro-drug codeine into its active form and the drug is therefore relatively inactive in CYP2D6 slow metabolizers.

CYP2C9 (cytochrome P450 2C9) is the primary route of metabolism for Coumadin (warfarin). Approximately 35% of the population are carriers of at least one allele for the slow-metabolizing form of CYP2C9 and may be treatable with 50% or less of the dose at which normal metabolizers are treated. Other drugs metabolized by CYP2C9 include Amaryl, isoniazid, ibuprofen, amitriptyline, Dilantin, Hyzaar, THC (tetrahydro-cannabinol), naproxen, and Viagra.

CYP2C19 (cytochrome P450 2C19) is associated with the metabolism of carisoprodol, diazepam, Dilantin, and Prevacid.

CYP1A2 (cytochrome P450 1A2) is associated with the metabolism of amitriptyline, olanzapine, haloperidol, duloxetine, propranolol, theophylline, caffeine, diazepam, chlordiazepoxide, estrogens, tamoxifen, and cyclobenzaprine.

NAT2 (N-acetyltransferase 2) is a second-step DME that acts on isoniazid, procainamide, and Azulfidine. The frequency of the NAT2 "slow acetylator" in various worldwide populations ranges from 10% to more than 90%.

VKOR vitamin K 2,3-epoxide reductase. Factor V Leiden and Factor II (Thrombin) are related to the 2C9/VKOR package in that the individual's genotype at this locus is a factor in predicting clotting risk.

Other genetic loci of known interest include C734A4, C734A5, C734A7, MTHFR genotype, methionine tetrahydrofolate reductase, homocysteine metabolism, TPMT poor metabolizer, UGT1A1, glucuronosyl transferase (active in metabolism of Labetalol, Morphine and Naloxone), S-methyltransferase, Factor II Thrombin, Celiac Disease Panel, Factor V, obesity-associated genetic loci, and ABCB1-P-glycoprotein. Some of these are experimental, some of proven impact on health care decisions. While the application is not limited narrowly to pharmacogenetic data, and may comprise genetic and metabolomic data more generally, the core GeneMedRx application server and programming is currently configured with a pharmacogenetic and pharmacological database as a preferred embodiment. not limited narrowly to pharmacogenetic data, and may comprise genetic and metabolomic data more generally, the core GeneMedRx application server and programming is currently configured with a pharmacogenetic and pharmacological database as a preferred embodiment.

The issues involved in interpreting genetic test reports and potential drug interactions are by no means simple. Some cytochrome P450s are expressed in multiple tissues (e.g., CYP3A4 has intestinal and hepatic sub-routes). A drug may be metabolized by one or both of the sub-routes. Drugs may also inhibit one sub-route preferentially. Selective entry into the brain is also controlled by independently expressed drug portals and metabolic enzymes of the blood brain barrier.

The particular tissue-specific sub-route by which a drug is metabolized is often not known because the data were collected before sub-routes were recognized. In the current algorithm, subroute information is utilized in predicting interactions; however, if no subroute information is available, one embodiment of the algorithm makes a conservative assumption that the drug is a substrate or inhibitor of all subroutes.

Given the complexity of the interactions between genotype, drug indications and other factors in delivery of personalized medicine, it should now be clear that a computerized tool of the kind disclosed here is essential for managing the required and associated medical information.

Turning now to the figures, FIG. 1 is an overview of the host software engines and servers 20, which are typically under control of a single operating entity, the Host System operator, who is responsible for constructing and maintaining the servers, databases, software and network interfaces. The Host System operator is reimbursed as shown in the figure, which includes five paypoints where financial transactions may be initiated and configured. These are paypoints 1, 2, 3, 4 and 5 as shown, and are directed to multiple market segments. Also shown are customer types 6 (full-use subscribers), 7 (fee-for-service users), 8 (conversion subscribers), 9 (sponsored users), 10 (contract laboratories), although these terms should be construed sensu lato and are not narrowly limited. For example, full-use subscribers may include wholesale users, and sponsored users may include promotional users. Certain customer types are interconvertible or overlapping, as will be described below.

Between horizontal lines 27 and 28, the host software is responsible for initiating the financial transactions and includes all Host System-compatible interfaces. Below horizontal line 28, outside software vendors may supply the required software, servers and user interfaces. Laboratory Billing System 25 and 3d Party Payor System 26 may also be supplied and operated by outside parties. The titleblock "3rd party payor" refers generically to private insurance carriers, granting agencies, government agencies and the like, where the financial transaction is indirect and might not involve the host software or servers directly. Although depicted once, the client laboratory block 25 and 3d Party Payor block 26 are indicative of a plurality of such entities.

Computing equipment of the Host System 20 comprises the Metabolomics Engine 21, datapipe (arrow) 29, the Genetic and Pharmacologic Database Editor module 17, Administrative server 18, datapipes 31, 32, 34, 35, 36, 41 and 51, and GUIs 30, 40 and 50, each of which will be explained subsequently in more detail. Datapipes are arrows indicating the flow of data in the system. Provision of hardware for computerized implementation of the system falls within conventional skills.

Integration of Host System functions may rely on hard-wired interconnections or on networked interconnectability. Network accessibility 12 is indicated in FIG. 1 and may comprise internet, intranet, wireless networking, and so forth. Web servers, wireless protocols, and GUIs suitable for connectivity of these sorts are well known in the art. Servers 17, 18, 25 and 26 may be remote servers and wirelessly connected to the Host System, which may be a single, integrated whole or can be distributed over multiple locations. Secure access, digital certificates, and encrypted web pages are known in the art. Recent computer security innovations such as reCaptcha, an open source project of Carnegie Mellon University, are also useful in implementing secure access.

The Metabolomics engine 21 comprises databases and logic modules programmed with software algorithms. While the following description includes particulars, it should be understood that the number of databases, the number of servers, and the location of data storage functions and logic modules, and so forth, may be modified by those skilled in the art while still consistent with the spirit and teachings of the invention. Database 22, encoded on a computer readable medium, is termed the Genetic and Pharmacologic Database (or "Pharmacogenomics database") and database 23, encoded on a computer readable medium, is the Administrative Records & Clinical Records Database, also termed simply the "Administrative Database". The Administrative Editor 18 handles business records, which are stored in Administrative Database 23, and related backoffice functions such as insurance claims processing, and validation and error tracing, and includes a user interface for authorized personnel. Database 23 is also the site for secure storage of patient medical records. Genetic and Pharmacologic Database Editor 17 is used to update biological, pharmacological, and pharmacogenetic look-up tables in the Pharmacogenomics database 22, and includes a user interface generally restricted to clinical specialists responsible for researching, maintaining and updating data extracted from current medical literature. The records entered in database 22 can include for example inhibition constants (Ki), inducers, metabolic pathways, sub-pathways, organ-specific pathways, interaction intensities (INTX), metabolic enzymes, correlations between markers for genetic polymorphisms (such as SNPs) and phenotypes, extensive references and annotations from the medical literature, related hyperlinks, drug generic and brand names, drugs, prodrugs, herbals, excipients, metabolite identifiers, drug interaction classifiers, drug metabolic routes, drug metabolic route weightings ($R_{1/1-n}$), uptake transporters, uptake transporter-substance interactions, organ-specific transporters, herbal interactions with drugs, patient characteristics, patient characteristic interactions with drugs and herbals, phenotype interactions with drugs and herbals, phenotype interactions with patient characteristic factors, drug therapeutic classes, therapeutic substitutes, composition of pharmaceutical mixtures, clinical status factors, drug label warnings, warnings from the medical literature, clinical trials, and cross-references, for example, and may be expanded to include new tabulations of data as deemed useful. Phenotypes include for example, "poor metabolizer", "normal metabolizer", "intermediate metabolizer", "ultra-metabolizer", "reduced heterozygous expressor", and so forth. Metabolic enzymes include for example cytochrome P450 enzymes CYP1A2, CYP2C19, CYP2C9, CYPNAT2 and CYP3A4 concerned with drug metabolism and p-glycoprotein transporters concerned with drug uptake and elimination. Among the algorithms programmed in the Metabolomics engine 21 are one or more PK predictive algorithms, which calculate the impact of phenotypic interaction, drug interaction, and clinical factor interaction on the AUC of pharmaceutically active compounds and metabolites, and makes predictive warnings if an adverse drug interaction is possible. Also included in the Metabolomics engine is a genotype-phenotype translator. These algorithms will be discussed in more detail in a subsequent section.

Lab Report Engine 24 includes programming for data entry functions, for interfacing with the databases of the Metabolomics Engine 21, and for assembling and transmitting laboratory reports. The contract laboratory GUI 30 is used for data entry and for controlling the production of Type I lab reports by the Host System. These reports, shown here as transmitted to user interfaces 30 and 40 via a network connection, contain laboratory-proprietary formatting and information such as a logo and contact information, patient information, and also genetic testing data. An algorithm in the Medical Metabolomics Engine 21 interprets or "correlates" the genetic test result with a phenotype and the Lab Report Engine incorporates the phenotype data into the Type I lab report, also storing a copy of the patient's record in Clinical Records database 23. Optionally included in the report is predictive content highlighting interactions of the reported phenotype with selected drugs where there is a likely interaction. The report takes into account that the patient may have multiple abnormal phenotypes. Each time it is accessed, this report is newly created by the system (using the Type I predictive algorithm) and reflect the most current patient genetic information and metabolic information in the databases. Access to the report is typically password protected. The lab report also may contain a live, sponsored-use hyperlink 43 (*) which will be discussed in more detail in the context of the paypoints.

Returning to a discussion of the paypoints and the multiple business models described in FIG. 1, we turn first to paypoints 3, 4 and 5. These financial transaction initiation points are linked to data transfers indicated by datapipe arrows 32, 31 and 33 respectively. The Host System operator is paid (Paypoint 4) by contracting laboratory 10, typically as part of a subscription for access to the Host System, for a service comprising the delivery of an enhanced laboratory report to the end user at user interfaces 30 and 40, or optionally by displaying the webpage report through a webserver on the laboratory's server 25. Note that the user is a customer for genetic testing services by the contracting laboratory and the contracting laboratory is in turn a customer of the Host System operator. The enhanced genetic test report includes a determination of a phenotype, where the phenotype is determined by a computerized interpretation of the raw genetic test data entered by the laboratory. The interpretation is made by the Lab Report Engine 24 using genetic and bioinformatic records on the Pharmacogenomics database 22. The Host System provides subscription services to multiple contract laboratories, but each test report is customized with the logo and contact information of the particular laboratory providing the testing, with such files and formatting as are required by the report-generating algorithm being stored in Administrative database 23.

The contracting laboratory is responsible for providing the results of a genetic test on a sample submitted by a patient, health care provider, or other party. To initiate a report of the test result, contracting laboratory 10 is provided with GUI 30 for accessing the Host System and enters patient identifier data and genetic testing result data into the Host System through datapipe arrow 31. This data is stored in the secure Clinical Records Database 23. Lab Report Engine 24 builds the report and transmits it to user interface 40, as represented by datapipe arrow 32. GUI 30 can also be used to print out a paper copy of the report for mailing to the customer or for reviewing and archiving the content. In another embodiment, the user can obtain this report by logging on to the laboratory server 25 and requesting it, the background operations of the Host System being seamlessly integrated into the foreground operations of the laboratory server.

The interpretation made by the Metabolomics Engine between the genetic test result and a metabolic phenotype is a service that can be billed as an interpretive or diagnostic laboratory service under a recognized CPT code ("Current Procedural Terminology code") or equivalent authority when performed under the supervision of a pathologist or recognized medical practitioner associated with the contracting laboratory. The Type I report also includes a detailed table showing the commonly prescribed drugs available where the user resides that interact significantly with the phenotype. This service is also billable as part of the Lab Report and reimbursement for access to the host system resources and predictive algorithm is passed on to the Host System operator.

In one preferred embodiment of the business model, upon delivery of the enhanced "interpretive" report to user interfaces 30 and 40, the laboratory server sets a flag that in turn results in an invoice being sent to a third party payer 26 (Paypoint 5), such as an insurance carrier, as indicated by datapipe arrow 33. All necessary information that the insurance company typically needs to process a claim will be included with the invoice. In this model, Paypoint 5 is external to the operation of the Host System, but is an inducement to use the Host System resources and serves as a supplemental profit source for the contracting laboratory. Contract genetic testing laboratories offering the enhanced power of the Metabolomics Engine have a marketable advantage because of greatly enhanced information they can report to their customers, information that would be very costly for any single laboratory to assemble, maintain, and deliver, even if the software had been commercially available. Insurance carriers offering coverage for genetic testing services, which can directly reduce medical costs by avoidance of adverse drug reactions, also have a marketable advantage. Use of existing CPT codes for automated interpretive services as a tool for billing for enhanced genetic test reports is a novel solution to a longstanding and unmet need in the industry. Prior art models include shopping cart-type fee-for-service billing and subscription billing. Here however, the billable event that drives the model is the fee for professional interpretation of the phenotype or the fee for professional predictive interpretation of potential drug-drug or drug-gene interactions, and by automating the billing, a broad range of pharmacogenetic interpretive services can be supported. Although the billable service accrues to the contract laboratory, and is paid by a third party payor, the revenue drives the subscription fees collected by the Host System operator to maintain the system.

Note that the end consumer is a customer of the contract laboratory and may be a patient or a health care professional, such as a physician. Patients in many states are authorized to order laboratory testing services in propria persona. Thus payment for interpretive services may be made in two ways, as distinguished by Paypoints 3 and 5. Either the contract laboratory is paid at Paypoint 3 directly by the customer for delivering the genetic test report or by an insurer indirectly at Paypoint 5. Serendipitously, this model allows health care providers, who wish to order genetic testing, to 'pass through' the costs of that testing and professional interpretation to insurance carriers (Paypoint 5). In this preferred model, the patient, health care provider, or end-use customer are not parties to the resulting financial transactions and are termed, "sponsored users" (9), who can access the report at interface 40. The laboratory may thus offer the enhanced report service at interface 40 to the patient or to an authorized health care provider at no charge under this model, a surprising and unanticipated solution to the problem of reimbursement for genetic testing services.

In the preferred arrangement, where the payor is a third-party and the invoice is submitted with a recognized CPT code, the market for genetic testing services is shown to increase over the direct fee-for-service model, and increased use results in reductions in overall costs of health care delivery and increased efficiencies. The result is a virtuous cycle. The rising cost of health care delivery, which includes an important component representing the increasing frequency and severity of adverse drug reactions and related complications and litigation, has been well established. Access to pharmacogenetics at the point of care is needed to help bring this escalating cost under control, but has been impeded by difficulties in discovering models and formulae for reimbursement. The problem of more widely providing genetic testing is solved by the reimbursement mechanisms described here—a third-party private insurance payor or a single-payer system is invoiced for those costs under accepted medical billing codes and accounting practices, allowing the health care provider to pass through those fees and access the data without an intervening fee-for-service, shopping cart, or subscriber transaction.

Paypoint 1 provides a parallel or alternative reimbursement pathway and illustrates a second aspect of the invention whereby real time, point of care access to bioinformatics can be funded. A full-service subscriber 6 interfaces with the Medical Metabolomics Engine 21 through Paypoint 1, as indicated by datapipe arrow 51 and GUI 50. Paypoint 1 can be configured for subscription access for full service customers 6, for example with annual or semi-annual dues, but also as a "pay-per-ping" fee for access. Paypoint 1 may also be marketed and priced for wholesale users, for example medical clinics with multiple patients and broadband access routed directly into each examination room. In this model, the patient uses passwords or access codes to control access, but a healthcare provider or physician can with the patient's consent, for a limited time, view the patient's genetic information on interactive user interface 50. This interface differs from interface 40 and 30 in that it allows the user to enter and model the pharmacogenetic consequences of various prescription and patient factors on a secure linkage, among other options and services, and to store the prescription data on-line. Full service user access includes guided assistance in evaluating the clinical effect of genetic polymorphisms, aid in assessing the impact of patient characteristics and factors such as pregnancy, alcohol, recreational drug use and smoking in the context of the patient's genetic makeup, predictive warnings about probable drug interactions not reported in the medical literature (based on the novel PK predictive algorithm), contextually specific assistance in choosing alternate drugs in a therapeutic category, annotated in-depth literature citations and hyperlinks, and ready reference to labeling, indications, package warnings, toxicology, and chemical information about drugs, herbals, pharmaceutical formulations, and mixtures, all in the context of current information about the patient's prescription regimen. The interactive Type II report capacity is novel in that it is generated "on the fly" (by the predictive algorithm) whenever accessed and thus increases the range of its predictions whenever PK or factor data is added to the database. The pharmacogenetic database is updated regularly by Editor function 17 so that the Type II report will always contain timely research findings. The Type II report and will flag any newly discovered or predicted interactions of immediate relevance to the particular patient's care. That is, an interactive report accessed in late September will likely contain new information not available in early June; an interactive report accessed while the patient is receiving one drug will contain unique information not included if the patient is switched to another drug; an interactive report accessed after the results of a genetic test are entered will contain a whole range of new information not available before the test result was entered, and so forth. Thus the report is a living, dynamic view of the most relevant patient-specific pharmacogenetic information at any given time and is accessible at the point-of-care by those with wireless devices or with an internet connection. This underlines the importance of designing reimbursement into the system.

Another novel feature of GUI 50 is access to a PK predictive algorithm in the Medical Metabolomics Engine 21. The PK predictive algorithms, unlike prior art efforts to present drug interaction data, are designed to identify drug-drug interactions, including interactions among three or more drugs, and to display the clinically significant interactions. The display integrates interaction studies from the clinical literature and the predictions of the PK predictive algorithm. The PK predictive algorithm also is designed to handle multiple polymorphism interactions, so that the significance of multiple alleles and multiple phenotypes is fully reflected in the predictions. As a novel and unexpected solution to a longstanding problem, this algorithm is effective even in the absence of clinical reports of a specific interaction, although when both a prediction and clinical study are available, priority is given to the medical literature in the choice of warnings displayed. The calculation is a mixed semi-quantitative and empirical estimate as explained below.

Also included are algorithms for adjusting dosage during changes in medication that factor in genetic polymorphisms, and hyperlinks for access to on-line information such as PDR and PubMed citations. The program will suggest specific therapeutic alternatives in a drug class when requested. The recommended alternatives are chosen by the program so as to avoid the potential DDI detected by the predictive algorithm.

The patient also can have the option of entering insurance information at Paypoint 1. A CPT code corresponding to the requested access level, is paired with insurer identifiers entered by the patient and contractual terms stored in the Administrative database 23. CPT codes are the most common currently used service descriptors generally accepted by insurers. These mutually-understood reimbursement code data are represented here by dotted arrow 52 between the Host System operator and one or more insurer servers 26. Thus, Paypoint 1 can be configured to permit direct invoicing from the Host System operator to an insurer, again a form of 'pass through' invoicing that allows the health care provider to order Type II pharmacogenetic interpretive services payable by the insurer. Under this model, the Host System operator provides interactive access and interpretive services to an authorized health care provider at no charge, or limited co-pay, to the patient or end user.

The host server 20 in this embodiment contains an insurance submodule, insurance information stored in the administrative database 23, and algorithms to detect reimbursable events at Paypoint 1 in GUI 50 and to process insurance claims. Certain insurance claims must be authorized in advance. All necessary information that an insurance company typically needs to process a claim will be included in a request for authorization to permit a service. The decision by the insurance company will determine how the Metabolomics Engine will process a transaction at Paypoint 1. The decision-making process is optionally represented by bidirectional arrow 52. If the insurance company authorizes the service, the system will proceed to offer the authorized service, for example access to a Type II report function or to a genotype interpretive function. If the insurance company denies authorization, however, the user will be held at Paypoint 1 pending selection of another option, for example an option to email a customer representative.

Once insurance authorization has been completed, the system processes the user's query. The insurance submodule, in conjunction with algorithms associated with Paypoint 1, will detect reimbursable services and assign the appropriate reimbursement codes, in conjunction with a billing server such as server 18. A preferred reimbursement code is a CPT code. The CPT code assigned will correspond to a generally approved fee schedule for professional interpretation of a genetic test result.

In another embodiment, users gaining first access to the Metabolomics Engine in the course of purchasing genetic testing services from a contract laboratory are converted to direct Host System customers. In this new model, "sponsored user" 9, viewing the lab report through user interface 40, is provided with a sponsored-use hyperlink or URL for access to user interface 50. The sponsored-use hyperlink (*), indicated by arrow 43, when accessed with a password and access code, opens up datapipe 41, which includes a selectable level of interactive access to the Metabolomics Engine at 44 under control of Paypoint 2. In this way, the contract laboratory customer is now directly accessing the Metabolomics Engine at GUI 50, which offers the user an opportunity to enter personal medical information and view multiple subpages with active links to in-depth information related specifically and contextually to the patient history. With this incentive, the customer can chose to continue as a sponsored user, for example for a trial period, or can convert to a subscription use (ie, as a "conversion subscriber" 8 or to a fee-for-access user 7), directly paying the Host System operator for the interactive access (Paypoint 2). The system can also offer links for ordering other genetic testing services from the referring lab, for example.

Importantly, the reports available at this level of service through GUI 50 include: interpretive Type II reports of contextual interpretation related to personalized information entered by the patient or end consumer and stored on the database, such as information about current prescription regimen, history of smoking, alcohol, and use of herbals. In contrast, the earlier-described Type I lab reports accessed through user interface 30 and 40 do not permit entry of patient-specific medical information related to treatment, drugs taken, or patient characteristics. The services offered can be endowed with multilevel permissions with corresponding costs (by configuring Paypoint 2), up to and including the full service benefits discussed in regard to Paypoint 1 above. Customers who convert in this manner become increasingly sophisticated in the use of pharmacogenetics in managing their medical care. By accessing GUI 50 while consulting with a physician, for example, the possible patient-specific risks of a new drug can be evaluated in the context of the patient's existing drug regime and genetic makeup before the prescription is written. Interactive access at 44 is thus seen as a natural step in conversion of the customer to full access at datapipe 51, whereby the customer becomes a direct customer of the Host System operator and accesses the system through Paypoint 1.

In another embodiment, when drugs are being prescribed that are subject to substantial genetic variability in metabolism, the algorithms of the Metabolomics Engine will advise the user of potential risks and suggest specific genetic tests.

The sponsored-user and conversion subscriber portal is secured by methods known in the art, using passwords, access codes and digital certificates, for example. The medical databases are encrypted.

FIG. 2 is a flow diagram illustrating the operation of Paypoint 1 of FIG. 1. As implemented on a computer system, for example the Host System of FIG. 1, an end user such as a physician, other health care professional or patient, accesses Host System 20 through GUI 50. The user enters a patient identifier and a password or other access information to gain access to a medical record stored on database 23.

The user then enters a list of a plurality of factors to be associated with the patient identifier on an interactive webpage, where the factors are selected from the group consisting of prescription drug usage(s), bioactive substance usage(s), and clinical factor(s). Metabolic phenotype information is also a factor, but is generally entered by a clinical laboratory under the supervision of a pathologist and not generally accessible to editing by the patient or end user. The genetic test data (genotype) entered by the laboratory is translated into a phenotype by the Medical Metabolomics Engine (21) and stored in the Clinical Records database. This establishes the patient's current drug and substance regimen and any significant clinical factors. On command of the user, the view is then updated with a prediction assessing the biocompatibility of the patient-specific data entered (ie. a Type II report). Also displayed are warning(s) of any predicted bio-incompatibility between the listed factors. The algorithm considers not only drug-gene interactions but also drug-drug interactions and drug-clinical factor interactions.

Typically, a predictive algorithm of the type disclosed herein, the Type II PK predictive algorithm explained in FIG. 5, is used to make the prediction. The service is flagged as a pharmacogenetic interpretive service for automated billing. At Paypoint 1, the system flags the operation in step 4 and automatically generates an invoice to a third party payor (step 4) or to a customer.

At Paypoint 1, access is a billable service, and the user has multiple choices in selecting a reimbursement method. In one option, the user can enter a financial instrument at a paypoint associated with said second graphical user interface. Of particular interest is a business model in which payment is received from a third party payor for the end user's access to the system. For example an insurance payor 26 may be billed by the Host System directly. One aspect of this is indicated in FIG. 1 by arrow 52, whereby the backoffice administration of the Host System operator has prearranged contractual understandings and a table of accepted billing codes that are used to monetize the value of the specific characteristics of the Type II report functions utilized by the user.

FIG. 3 is a flow diagram illustrating the operation of Paypoint 2 of FIG. 1. Paypoint 2 is more complex but also involves GUI 50. A major advantage of this automated business method is the ability to convert a contract client's customer to a direct customer of the Host System, while providing win-win value to the client laboratory. As implemented on a computer system, a client laboratory in the business of providing genetic testing services accesses the Host System 20 at first GUI (GUI 30). The client typically has a contract or subscription agreement to access the Host System. In step 1, the client (typically a laboratory technician) enters a patient identifier and a genetic test result (typically a genotype or "star data") associated with the patient and stores that information in Clinical Records database 23. The system merges records associated with a single patient identifier. The client then enters a command to the host server that generates a test report (Type I) using host system resources (step 2); the test result includes a phenotypic interpretation of the genotype(s), a list of drugs for which the drug's metabolism is likely to be adversely impacted by the phenotype (ie. potential drug-gene interactions), a hyperlink to a second GUI (GUI 50), and a password or access codes whereby the customer (such as a patient, physician) can access the Host System (20) directly. Typically, in step 3, the client transmits the report to the customer 9, optionally via a Host System webserver. Encryption is commonly used to secure the data during transmission and storage of passwords.

Operation of the PK predictive algorithm used in preparation of Type I reports is explained in more detail in FIG. 4.

Figure 10:
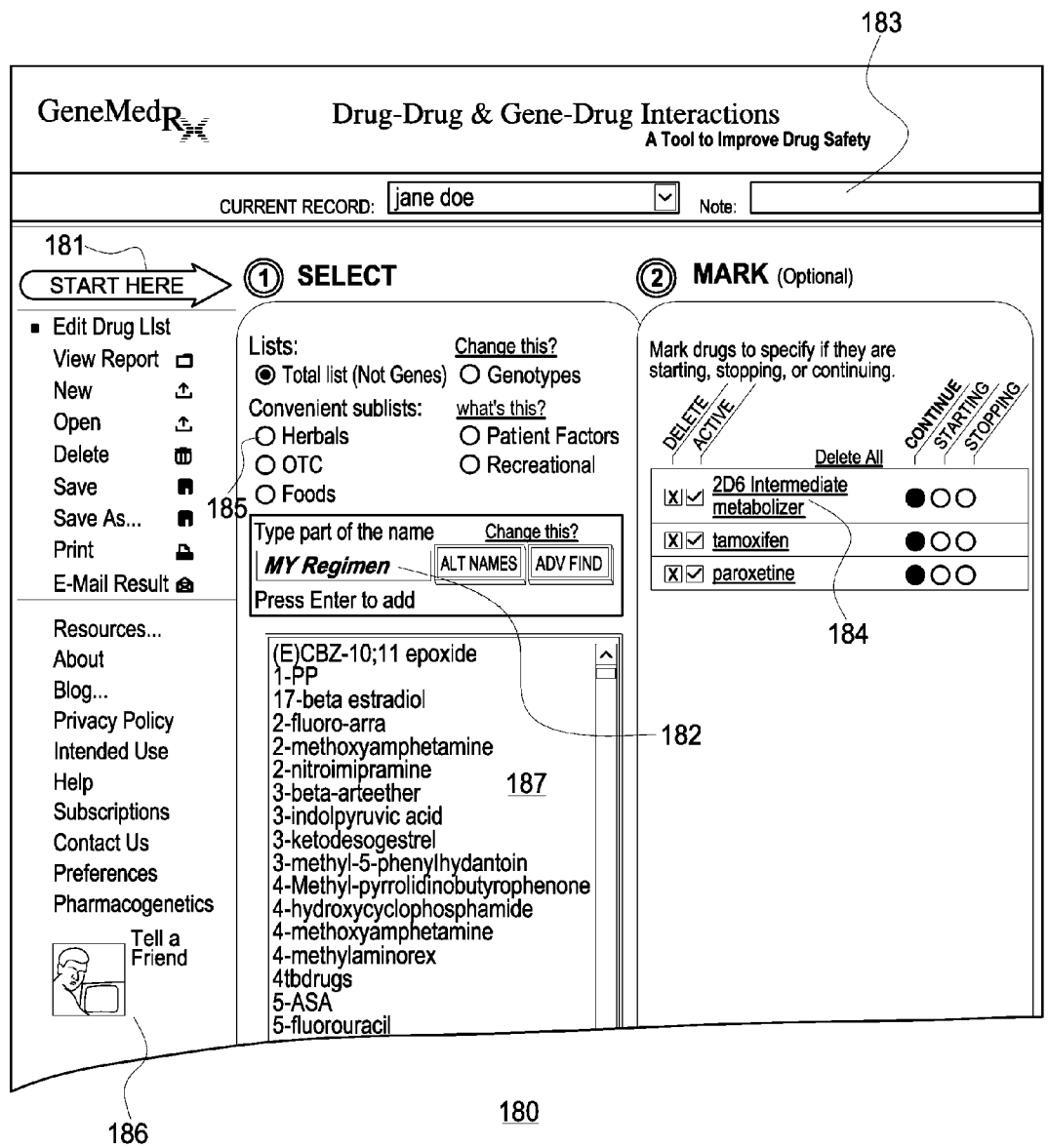
FIG. 10 is a detail of an interactive webpage for entering personal information and current drug regimen.

In step 4, when the customer 9 accesses the Host System directly at GUI 50, and enters the patient identifier and password, the Host System provides an interactive webpage (the opening screen for a Type II report). This screen is illustrated in FIG. 10. The user has the option of entering a plurality of clinical factors associated with the patient identifier, for example prescription drug(s) and bioactive substance(s) taken, and other clinical factor(s) (ie. "patient characteristics") such as age, pregnancy, smoking, and so forth. Customers 9 may have restrictions on levels of access. In one embodiment the customer is not authorized to delete or add phenotypes. This prevents the user from giving unauthorized access to guest users. After entering the list of drugs and other factors, the patient can give his or her healthcare providers access to the complete patient record from any computer or PDA with internet access. The medical record is stored on the Host System server and requires a password or other access code for authorized access.

A Type II PK predictive algorithm (discussed below, FIGS. 5-7) is then run. For any metabolic pathway associated with a drug or substance on the list entered by the user, the system identifies any drug-drug, drug-bioactive, drug-clinical factor (or "drug-patient characteristic"), drug-phenotype and substance-phenotype potential "interaction pair(s)", and identifies the impacted substrate (the "victim"). One drug (the "culprit"), for example, will inhibit the metabolism of another, resulting in greater exposure of the patient to the victim drug. An overdose can occur if the drugs are co-administered. The algorithm then calculates a change in the AUC of the impacted substrate and annotates a table with this information (see FIG. 6, subroutine A, and FIG. 8). The table may also contain hierarchically selected warnings drawn from the literature or based on the PK algorithm result (FIG. 7, subroutine B). This information is assembled into a webpage (a Type II report) at GUI 50 and presented to the customer 9. The exchange is flagged at Paypoint 2 and the information about the transaction is forwarded to a billing server.

Paypoint 2 also offers the user the ability to configure the transaction. In one model for reimbursement, the customer is offered several methods of paying for the data ranging from subscription and "pay-per-ping" with a credit card to wholesale bulk access at a dedicated GUI. A preferred reimbursement model permits the customer (often either the clinic or a physician) to 'pass through' the cost of the interpretive access and consultation to a third party insurer. In this case, an interactive screen associated with Paypoint 2 allows the user to enter insurance information. Customers of type 9 may convert to customers of type 8, 7 or 6 by this method.

Note that in this model the customer is essentially handed off from the client laboratory to the Host System operator. Given the synergies of the model, the client laboratory also benefits by this arrangement.

FIG. 4 is a flow diagram illustrating the production of a Type I report and the operation of Paypoints 3, 4 and 5 of FIG. 1. In this embodiment, a "pass-through" cost model for the client laboratory is developed.

The client laboratory accesses the Host System 20 and enters a patient identifier, laboratory identifier, and a genetic test result in a database. A command from the client causes the Lab Report Engine 24, operating with the Metabolomics Engine 21, to produce a Type I laboratory report formatted with the client's logo. The test report includes a phenotypic interpretation of the genetic test result and a list of drugs likely to be associated with a Change % AUC based on the phenotype. This is a drug-gene interaction report. The report is then securely transmitted to the consumer, either directly by the Host System at GUI 40 or by the laboratory server. The laboratory flags the transmission (step 3) as a billable service either at Paypoint 5, submitting an invoice for reimbursement to a third party payor for the phenotypic interpretation service, or at Paypoint 3, submitting an invoice to the customer. In the preferred method, (step 4) the subscribing laboratory recovers the costs of accessing host system resources by generating a "pass-through" billing based on a reimbursement code, such as a CPT code, corresponding to a generally approved fee for a diagnostic pathology fee, which according to a preferred embodiment of the method, is paid by the patient's insurance. The client laboratory pays the Host System operator for access to the host system.

The steps of the PK predictive algorithm in FIG. 4 illustrate the use of phenotype data to calculate CP for each drug. In step B, drugs are selected for the sublist from the database (22) by therapeutic class, Medicare Part D reimbursement eligibility, regulatory approval specific to the jurisdiction, frequency of prescription usage data, and so forth. The list is unbundled by adding components of drug mixtures, prodrugs, enantiomers and metabolites. Drug-gene interaction pairs are then identified. Literature concerning the phenotype is searched to determine the intensity INTX of inhibition or induction associated with the impacted metabolic route. Parallel alternate metabolic pathways are also evaluated for FRACTION $R_{1/1-n}$ (metabolic throughput on the affected route R divided by total metabolic throughput by all parallel pathways $R_{1-n}$). The equation for CP "change points" can then be solved:

$$CP = INTX * (R_{1/1-n}),$$

This calculation is performed only if the patient phenotype is abnormal. For each potential victim drug, the net affect of all phenotypes is calculated by summing CP:

$$\Sigma CP = (CP_{R1} + CP_{R2} + \ldots CP_{Rn})$$

The calculations are stored in a summary table of results. The value $\Sigma CP$ is converted to a Change % AUC using a look up table such as shown in FIG. 8. If the change in CP is less than a threshold level and there are no clinical warnings in the notes in the database, then the drug is deleted from the sublist. This process is repeated for all drugs and the drugs remaining on the sublist are tabulated for presentation in the Type I lab report as shown for example in FIG. 9. The Type I lab report typically consists of a patient identifier, laboratory identifier, a phenotypic interpretation of the genetic test result(s), and the predicted drug-gene interactions from the sublist, also showing predicted Change % AUC (up or down). This report can be formatted so that it appears consistent with the look of other documents or webpages of the client laboratory.

FIG. 5 is a flow diagram outlining the major operations of a PK predictive algorithm used in the preparation of Type II reports of the examples. In step 6, any potential interaction pairs that can be associated with a drug interaction are identified. These include drug-drug, drug-bioactive, drug-clinical factor, drug-phenotype, and substance:phenotype interactions.

In step 1, a factors list is entered and tabulated. This list consists of drugs, bioactives, factors taken from the clinical history, and genotypes or phenotypes. In step 2, the list is then factored or "unbundled" by converting any drug mixtures to their individual drug components, identifying prodrugs, replacing racemic substances which have relevant enantiomers with the enantiomers (for example warfarin has r and s isomers with markedly differing metabolism and bioactivity), and adding to the table any pharmacologically active metabolites. A class membership may also be identified. Typically the genotype is already in the clinical records database and the translation to phenotype has already been made, but it may be done so in step 3 if not already completed.

In step 4, inhibitors and inducers on the list are identified. Inhibitors and inducers may act on more than one metabolic route. An intensity index expressing the degree of induction or inhibition of each metabolic route is also tabulated. Victim substances are then identified in step 5 and associated with the metabolic routes. These operations are performed by accessing a list of the metabolic pathways for each substance, and then ascertaining all inducers and inhibitors of those pathways contained in the factors list. The resulting table contains all "interaction pairs" relevant for each metabolic pathway. Each interaction pair includes one victim and one culprit substance or factor (step 6).

The computer then makes, in step 7, quantitative interaction calculations for each interaction pair:

$$CP = INTX * (R_{1/1-n}),$$

where CP" is the "change point" score for each metabolic route R of each drug identified as the victim in the interaction pairs table, INTX is an intensity of interaction index derived from clinical and laboratory studies of individual substances and genes (or factors), $R_{1/1-n}$ denotes $R_1/(R_1+R_2 \ldots R_n)$, where $R_n$ refers to one of the set of parallel metabolic routes taken by the substance and $R_{1/1-n}$ is the proportion of metabolism that flows through pathway $R_1$, and so on. This quantifies the relative change in AUC of the victim substance resulting from one interaction on one metabolic pathway. The change point score CP can be positive or negative, representing the opposing effects of induction and inhibition.

In the next calculation, step 8, the CPs for all metabolic routes R for each interaction pair are summed:

$$\Sigma CP = (CP_{R1} + CP_{R2} + \ldots CP_{Rn})$$

and the calculations are stored in a summary table of results.

For each drug or substance, the change in AUC can be complex, resulting from multiple interactions. In a preferred embodiment, for each interaction pair, a $\Sigma CP$ score is calculated that quantitates one particular interaction, and the $\Sigma CP$ scores of all the interactions are then summed across all pairs for a common victim to determine the net change in drug blood level and clearance for the victim of multiple interactions.

Step 9 converts raw change values to Change % AUC values for each victim substance (See FIG. 8. FIG. 8 is representative of the look-up process whereby $\Sigma CP$ is converted to a percent change in blood level). When the results are compared with published clinical studies from the literature, this composite method is surprisingly effective at making accurate predictions. We have found that these results correlate well with literature studies where available. The PK predictive algorithm's accuracy can be tested by comparing the AUC changes it predicts for pairs of interacting drugs with literature reports of clinical studies of the same pairs.

In step 10, the algorithm may comprise a subroutine for collating literature-derived reports related to each interaction pair identified. Relevant clinical notes in the database bibliographical records are called up and attached to the main results table. Literature clinical study notes germane to the substance class or "class membership" are also identified if desired. The algorithm creates a list of the clinical studies and their associated scientific confidence ratings. In instances where research confirms the absence of interaction, an appropriate note presents this information.

The result is a prediction of the effect of the interactions on the victim substance AUC, its blood level and clearance time, as reflected in the change in its pharmacokinetics as a result of the second impacting "culprit" substance or factor. The prediction is made even if supporting clinical studies are not available.

In subroutine A (FIG. 6) the impact of each metabolic route $R_n$ on the victim substrate is quantified as the product of the interaction intensity INTX with the fractional metabolism of the victim by the metabolic route over the total metabolism by all parallel metabolic routes $R_{1/1-n}$.

FIG. 7 is a detail showing the steps of subroutine B. Subroutine B compares the prediction of an interaction with literature citations stored in the databases. The warnings are ranked by severity and the most significant warning is displayed.

The warnings are displayed according to the following rules. After tabulating all warnings according to priority from highest to lowest, the highest priority warning on the list is displayed on the Type II interaction report.

A. Major interaction warnings based on a clinical study
B. Reported interaction based on a clinical study
C. Major interaction warning predicted by the PK predictive algorithm
D. Reported lesser interaction based on the PK predictive algorithm FIG. 8 shows a table used in the PK predictive algorithm to convert $\Sigma CP$ to a percent change in AUC. Showing are ranges of point scores corresponding to $\Sigma CP$ calculations (81, column 1), an interpretation of the predicted qualitative effect (82, column 2), a change index used to build column 2, and a predicted % change in AUC (84, column 4). Note that the Change % AUC can be up or down (plus or minus sign).

Returning to FIG. 5, in Step 11 the Host System builds a webpage that reports the Type II predictive analysis back to the user. The user may in turn modify the input by selecting an alternate drug not linked to an interaction (and potential ADR) and run the analysis again. All clinical data is stored in the system.

A refinement in the PK predictive algorithm of FIG. 5 is as follows. Class memberships of the victim and culprit drugs are identified. The database is then searched for other members of the same class membership. The commonality of these class memberships is a shared side effect. If found, the two drugs or substances of the class are annotated in the report. This is done because side effects can be additive if the two drugs are co-administered. Thus the algorithm can also detect DDIs even when a genetic interaction is not relevant.

Interestingly, the patient can share this service with the physician, or vice versa. During an office visit, patient and physician can model and discuss alternative therapies and use the system to explain any unexpected adverse reactions when the patient tries a medication, ordering genetic testing if necessary. The system will update the Type II report each time it is accessed.

Prior art reports do not contain a list of drugs sorted by drug class that have been shown by predictive algorithm or review of the clinical literature to interact with the listed phenotype. Instead there is a black-box warning, "Do not alter the dosage amount or schedule of any drug you are taking without first consulting your doctor or pharmacists." This warning is necessary given the risk of DDI and ADR in this patient phenotype, but is of little value at the point of care in prescribing safely. There is thus a need for improvement over the prior art, a need met by the algorithms of the current invention.

Avoidance of a major ADR is a medical cost savings, but requires the 'pass through' reimbursement functions of the system to be generally accessible to physicians. In this system, the user is again interfacing directly with the Metabolomics Engine at GUI 50 and may be preferred "full-subscription" customers 6, "conversion" subscribers 8, "trial use" or "sponsored use" users 9, or "fee-for-service" customers 7, for example. Paypoint 2 is provided with a means for flexibly selecting a suitable payment option, including insurance options for pass-through of costs, thus ensuring that the drug interaction warning and supplemental information is made available where and when needed.

In a preferred embodiment, this advanced level of interactive information is made accessible to the end user through a hyperlink or access code appended to a Type I Lab Report such as is generated by the Lab Report Engine at GUI 30 or 40. The hyperlink is a link to interactive GUI 50 with more detail on 1A2 Hyperinduction related to any pair of drugs (or drug:herbal pairs, etc.), and a user can proactively enter their own prescription information to determine whether there is a contraindication before prescribing or taking them.

FIG. 9 is a view of a sample Type I lab report 170 with sponsored-use hyperlink 173. The report includes an interpretation of a phenotype 171 associated with the below—named genotype. In this example a 2D6 poor metabolizer is associated with a CYP2D6 *3/*4 genotype, as determined by genetic testing. At the bottom of the report, an extended list 172 (here truncated) of drugs of predicted interactions with the named phenotype is given, allowing the end user to identify any potential concerns for follow up.

Also provided is a hyperlink 173 for more personalized information. In this embodiment, the hyperlink corresponds "sponsored user" hyperlink of the type shown in FIG. 1, element 43 (*) and is linked to GUI 50 at Paypoint 2. At GUI 50, various structured types of payment for access are available, but by providing a trial or sponsored service at Paypoint 2, genetic testing customers 9 are converted to use of the Host System. In a preferred business model, a "sponsored user" hyperlink 43 takes the consumer, whether a physician, patient, or lay caregiver, to an enhanced graphic user interface (GUI 50) with improved paypoint capability (Paypoint 2). With hyperlinks of this sort, a trial period is offered so that customers discovering the enhanced services of GUI 50 through the sponsored user hyperlink access will be encouraged to try out the service and convert to a direct financial relationship with the Host System operator, opting for the full or layered service of Paypoint 1. Payment options can comprise a fee-for-service, subscription, trial, discount, wholesale, or other relationship whereby the user accesses the tools of GUI 50. In a preferred embodiment, Paypoint 1 offers a 'pass through' feature convenient for medical health care professionals who need access to pharmacogenetic testing data, such as when writing prescriptions, but who would not choose to pay for those services when undertaken on a patient's behalf. The patient can, for example, access the service while meeting with a health care provider, to ensure that any prescriptions written is likely to be compatible with other patient factors already entered in the system, and optionally, bill the on-line consultation services to an insurer.

The predicted drug-drug interactions have been reassorted by therapeutic class and when accessed, the list is much more comprehensive, spanning 5 pages (not shown). The report states, "These genotype-based drug metabolism tables are generated from the GeneMedRx drug interaction computer program, which is based on a compilation of information found in the medical literature and interpreted by the use of a computer algorithm. The tables are to be used as a tool to provide decision support, consultation and advisory input to clinical care by medical professionals." Contrast this with the black box warning above.

FIG. 10 is a representative view of a interactive screen 180 titled "Drug-Drug and Gene-Drug Interactions" and begins with a note to "start here" (181). This is provided as an example of a portal to the Type II GUI. The end user (a patient or patient's representative) begins by entering a patient regimen at window 182. The selections can be entered by selecting factors from the list shown in window 187. The regimen consists of prescription drugs being taken and other patient factors as may be configured by the system operator. Notes regarding any relevant clinical history can also be entered in window 184. Information about the patient's phenotype is displayed at 184. The phenotype is generally entered by a contract laboratory providing genetic testing services and is stored on the Host System without need for re-entry by the patient. Sublists (e.g. "herbals", bullet 185) are provided for entry of other factors, such as herbals, over-the-counter drugs, and foodstuffs known to interact in drug metabolism. There is also an option 186 to make referrals. Once this information is entered, we turn to FIG. 11 for the next step—step three.

Figure 11:
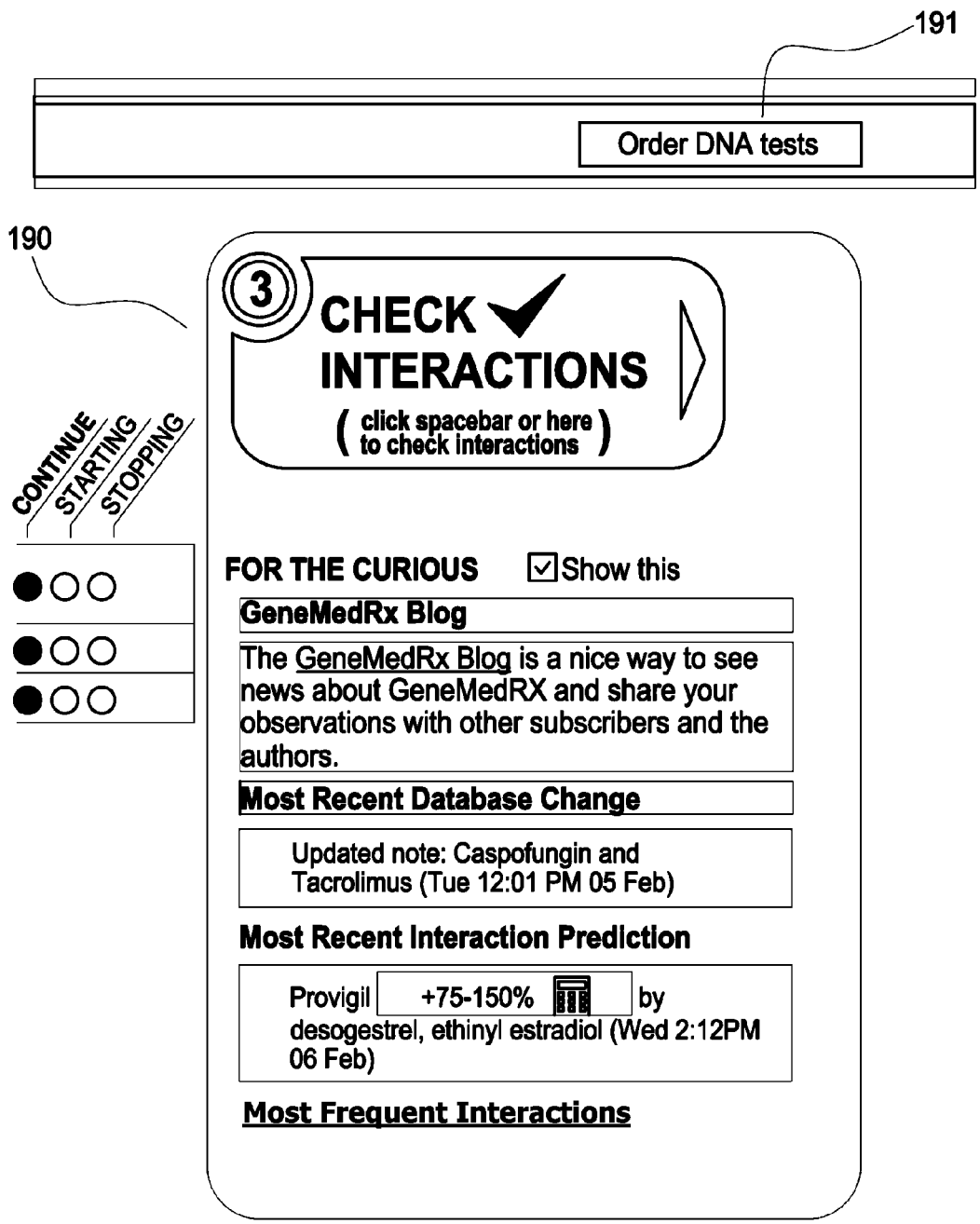
FIG. 11 is a detail of an interactive webpage containing a command interface for preparing a Type II report.

FIG. 11 shows a "check interactions" button 190 displayed on the GUI 50 interactive website. Also shown is a convenience function 191 for ordering genetic testing services. In one embodiment, this ordering function is a referral of the user back to the laboratory that provided the genetic test result which in turn brought the user to GUI 50. It may also include links to other genetic testing services, such as paternity services.

Figure 12:
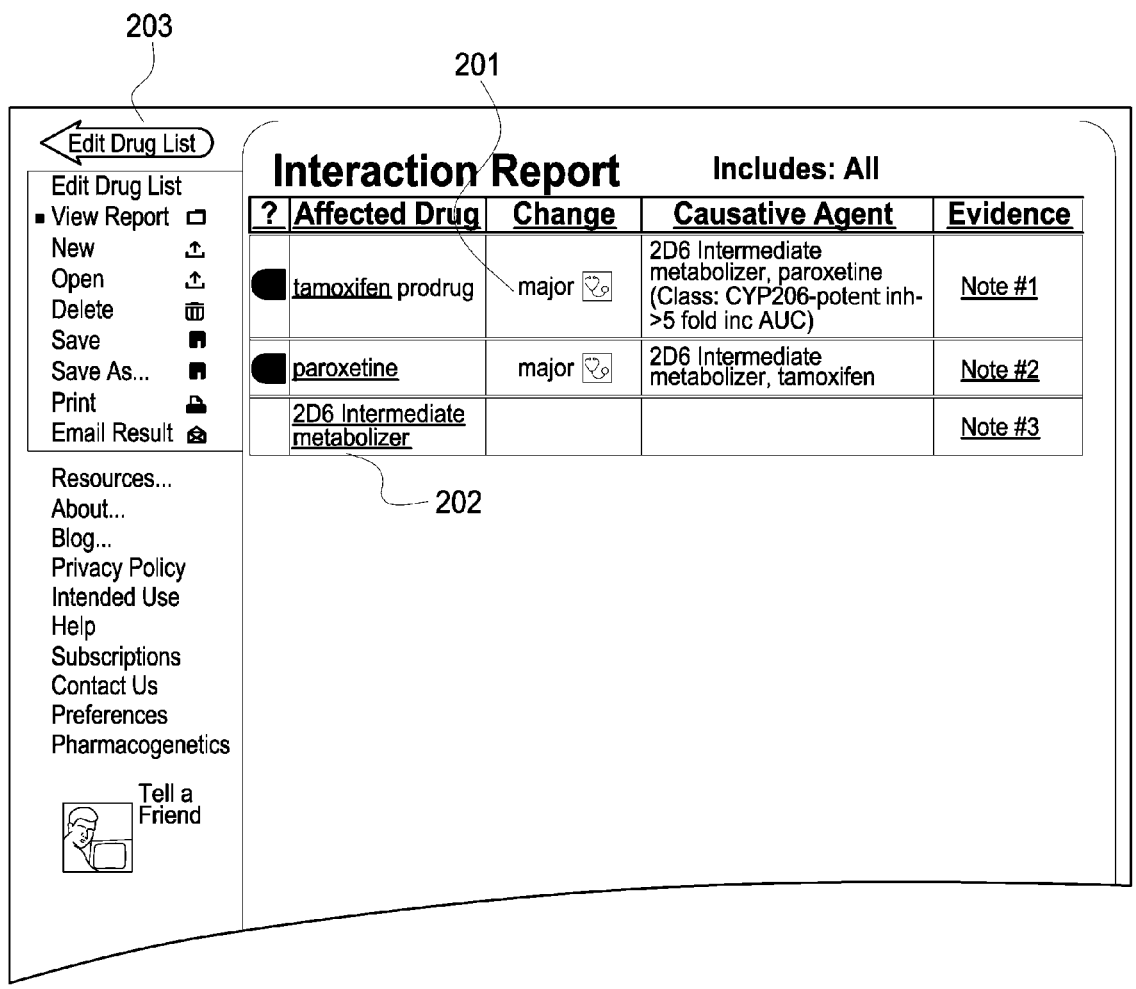
FIG. 12 is a detail of an interactive Type II report showing a DDI in a 2D6 intermediate metabolizer.

FIG. 12 is an "interaction report" (ie. a Type II report) generated by GUI 50. The report 200 is sent to the user in response to a command to check interactions as shown in FIG. 11. This Type II functionality is characteristic of GUI 50. The report describes a major interaction 201 (known in the clinical literature) between tamoxifen and paroxetine, also predicted by the PK predictive algorithm, for a 2D6 intermediate metabolizer phenotype 202. The interaction between tamoxifen and paroxetine is both a drug-drug interaction, paroxetine the victim and tamoxifen the culprit, and also a drug-gene interaction; both drugs are impacted by the 2D6 intermediate metabolizer phenotype. Added information about the mechanism and notes to hyperlinks for in-depth information and self-directed search are also provided. Note that the user can click on a hyperlink 203 to return to and enter or edit the list of drugs substances (and other factors) that are part of the patient's current treatment regimen, perhaps selecting an alternate drug.

FIG. 13 is a webpage 210 used at Paypoint 1 or Paypoint 2 to configure reimbursement options. The user is asked for more information which corresponds to a market segment. By selecting the appropriate bullet from the list 211 (bracket), the user is directed to follow-on pages with the appropriate functionality. Data is entered that allows the system to process financial transactions covering reimbursement for the system's data exchanges with the user. A patient who selects bullet 212, for example, is offered additional choices of credit card or entry of insurance information, and the credit card or insurance is then verified for authorization to conduct the transaction. Various trial subscriptions 213 are also optional, both for medical professionals and for patients. After completion of the financial information, the user is then directed to a start page for selection of permissible tasks. Not all users have equal access to core and extended functionality. Users who have a sponsored subscription will be directed to a webpage to enter the appropriate passwords or access codes before being granted access to system functions.

In one aspect, the invention is directed at a Type II predictive algorithm and apparatus or method for performing the operations of the predictive algorithm. The invention comprises a method or apparatus for predicting a substance-factor interaction, including drug-drug and drug-gene interactions, and comprises steps for a) providing a graphical user interface, a host system, and a database, wherein said graphical user interface is configured for:
   i) accessing a patient record in said database, said patient record comprising a patient identifier and a first patient phenotype;
   ii) entering one or more factors into a list associated with said patient identifier, wherein said one or more factors are selected from the group consisting of prescription drug, substance, and personal characteristic;

b) providing a predictive algorithm implemented on said host system, said algorithm having instructions for performing operations on said database, said patient record and said associated list, wherein said operations comprise:
   i) unbundling the list, thereby forming an unbundled list;
   ii) determining each factor on the unbundled list that is an inhibitor or an inducer; and assigning an intensity index INTX to each said inhibitor and inducer;
   iii) selecting from the unbundled list a sublist of victims, where a victim is a factor having the property of being a metabolic substrate of one or more metabolic routes Rn;
   iv) identifying each metabolic route associated with said sublist of victims;
   v) identifying each interaction pair associated with said each metabolic route, each interaction pair consisting of a victim and a culprit;
   vi) for each victim of said each interaction pair; calculating a CP score by multiplying an intensity index INDX associated with the culprit times a metabolic throughput proportion R1/1–n, where R1/1–n is calculated as the metabolic throughput of said each metabolic route Rn divided by a sum of the throughput of all metabolic pathways acting on the victim in parallel;
   vii) summing the CP scores for each victim and for each interacting pair, and tabulating the sums ΣCP;
   viii) computing a change percent AUC for each victim and for each interacting pair;
   ix) displaying a Type II report tabulating patient identifier, patient phenotype, factors entered in said list, and change % AUC for each victim; and,
   x) flagging the Type II report as a billable service.

The invention is adapted for predicting interactions between a plurality of substance-factors where there are a plurality of victims. In one Type II method, the sublist of victims comprises a plurality of victims. In another Type II method, the patient record comprises a plurality of patient phenotypes. In another Type II method, the substance-factor interaction comprises a drug-gene interaction, a drug-drug interaction, or a combination thereof.

Type II methods also can include provision for identifying and displaying literature notes and warnings. The algorithms further comprise a subroutine, said subroutine having instructions for performing operations on said database, said patient record and said associated list, wherein said operations comprise:
   i) accessing the database and identifying notes or warnings compiled from published reports of an interaction between said first victim and said culprit;
   ii) if no notes or warnings compiled, reporting said change percent AUC identified with said first victim and said culprit; and,
   iii) if notes or warnings compiled, reporting said notes or warnings identified with said first victim and said culprit.

Type II methods can also include provision for assessing class membership, wherein the operations further comprise:
   i) for any prescription drug or substance on said list, accessing the database and identifying a class membership, wherein said class membership is defined by a side effect produced by all members of the class;
   ii) for any class membership identified herein, accessing the database and identifying any factors from the list having said class membership in common; and,
   iii) reporting said factors in common, with a note advising that said side effect can be additive.

Type II methods include tools for making alternate drug selections. The operations further comprise:
   i) for any potential interaction pair for which said change percent AUC exceeds a threshold value, accessing said database and identifying a therapeutic class associated with said first victim;
   ii) identifying an alternate member of said therapeutic class and calculating an alternate percent change AUC for the alternate member;
   iii) reporting the alternate member in a listing of interactive selection of alternates if the alternate percent change AUC does not exceed a threshold value.

The methods and apparatus also include provision for generating a Type I lab report, which will predict a drug-gene interaction when given a phenotype and a list of drugs. The method or apparatus comprises a graphical user interface, an host system, and a database, wherein said graphical user interface is configured for:
   i) entering a patient record in said database, said record comprising a patient identifier and a first patient phenotype;
   ii) providing a predictive algorithm implemented on said host system, said algorithm having instructions for performing operations on said database, said patient record and said associated list, wherein said operations comprise:
   iii) accessing a list of drugs on a database, said drugs comprising prescription drugs and substances, and unbundling the list, thereby compiling an unbundled list;
   iv) determining an inhibition or an induction of at least one metabolic route Rn associated with said first phenotype; and assigning an intensity factor INTX to said inhibition or induction;

v) selecting from the unbundled list a sublist of victims, where a victim is a member of said unbundled list having the property of being a metabolic substrate of said metabolic route Rn associated with said first phenotype;

vi) for each victim in said sublist, calculating a CP score by multiplying an intensity index INDX associated said inhibition or induction of said at least one metabolic route Rn associated with said first phenotype times a metabolic throughput proportion R1/1−n, where R1/1−n is calculated as the metabolic throughput of said metabolic route Rn divided by a sum of the throughput of all metabolic pathways acting on the victim in parallel;

vii) from the CP score of the preceding step, computing a change percent AUC;

viii) discarding any drugs in the sublist if the change % AUC is below a threshold value; thereby forming a summary table;

ix) displaying a Type I report tabulating patient identifier, patient phenotype, laboratory identifier, and change % AUC for each victim in said summary table; and, x) flagging the Type II report as a billable service.

Type I methods are also adapted to predicting a drug-gene interaction for a plurality of patient phenotypes, and said operations comprise calculating a ΣCP score for each victim, where said ΣCP score is the sum of the CP scores over said plurality of phenotypes, and computing change % AUC for each victim from the ΣCP score in said summary table.

The methods are also adapted as business methods. In one embodiment the invention is a business method for obtaining reimbursement for pharmacogenetic interpretive services, which comprises:

a) implementing a billing server configured for detecting a flag associated with a service of claim 1;

b) invoicing a payor associated with the patient identifier, and optionally, said payor is a third party payor and said billing server comprises an insurance submodule.

In another embodiment the invention is a business method for obtaining reimbursement for pharmacogenetic interpretive services, which comprises:

a) implementing a billing server configured for detecting a flag associated with a service of claim 7;

b) invoicing a payor associated with the patient identifier, and optionally, said payor is a third party payor and said billing server comprises an insurance submodule.

The methods are adapted for operation at Paypoint 1. Conceived is a business method, as implemented on a computerized host system, for obtaining automated third-party reimbursement by providing pharmacogenetic interpretive services for preventing a possible adverse drug reaction, comprising the steps of:

a) providing a first user with a means for accessing a host system and a means for entering a patient record comprising a patient identifier of a patient and a genotype associated with said patient identifier, and thereupon b) on command of said first user, translating said genotype into a phenotype and entering said phenotype in said patient record;

c) providing a second user with a means for entering a plurality of factors into the patient record, wherein the factors are from the group consisting of prescription drug(s) prescribed, substance(s) used, clinical factor(s);

d) upon command of said second user, computing a change % AUC for any interacting pairs of factors entered, computing a prediction warning of a potential bioincompatibility between said interacting pairs, wherein said prediction is made by a PK predictive algorithm, and displaying a report; and, e) flagging the prediction as a billable service; and wherein the method is further characterized in that reimbursement is made according to a prearranged fee schedule between an operator of the host system and a third party payor contracted by said patient to pay for said billable service.

The methods are also adopted for operation at Paypoint 3, 4 and 5. Conceived is a business method, as implemented on a computerized host system, for obtaining automated third-party reimbursement by providing pharmacogenetic interpretive services for preventing a possible adverse drug reaction, comprising the steps of:

a) providing a first user with a means for accessing a host system and a means for entering a patient record comprising a patient identifier of a patient and a genotype associated with said patient identifier; and thereupon b) on command of said first user, translating said genotype into a phenotype and entering said phenotype in said patient record;

c) upon command of said first user, selecting a list of drugs, computing a change % AUC for any interacting pairs of factors entered, computing a prediction warning of a potential interaction between said drug and phenotype, wherein said prediction is made by a PK predictive algorithm; and preparing a Type I lab report comprising a pharmacogenetic interpretive service;

d) upon command of said first user; transmitting said report to a customer, wherein said customer is a customer of said first user and flagging said transaction to a billing server operated by said first user;

e) receiving a reimbursement from said first user for access to said host system;

wherein the method is further characterized in that the billing server operated by said first user automatically bills for said pharmacogenetic interpretive service. Optionally, the billing server is further characterized in that said billing server automatically bills a third party payor contracted by said patient to pay for said pharmacogenetic interpretive service.

Customer conversion methods are also conceived. In one embodiment, we conceive a business apparatus for obtaining automated reimbursement for pharmacogenetic interpretive services, said apparatus comprising a computerized host system operated by a host system operator and having a means for data storage, a means for data processing, a means for networking, a first graphical user interface for access to the host system by a first user, a second graphical interface for access to the host system by a second user, wherein said apparatus is configured with means for:

a) under control of said first user, entering and storing a laboratory identifier, patient identifier and a genetic test result comprising a patient genotype in a patient record on said first graphical user interface of said host system, said first user being a laboratory with a client relationship with said host system operator;

b) on command of said first user, performing a phenotypic interpretation of said genotype entering said phenotype in said patient record on said host system;

c) on command of said first user, using a first predictive algorithm resident in said host system to prepare a predictive drug-gene interaction report (a Type 1 report);

d) under control of said host system operator, appending a hyperlink to said predictive drug-gene interaction report, said hyperlink having the property of linking to said second graphical user interface;

e) on command of said first user, transmitting said predictive drug-gene interaction report with appended hyperlink to said second user, said second user being a patient or a responsible medical care provider;

f) under control of said second user, opening said second graphical user interface when said second user accesses said appended hyperlink;

g) under control of said second user, editing said patient record to add a list of factors to be associated with said patient identifier, wherein said factors are selected from the group consisting of prescription drug, substance, and clinical factor;

h) on command of said second user, using a second predictive algorithm resident in said host system to prepare a predictive drug-drug and drug-gene interactive report (a Type II report), flagging said predictive drug-drug and drug-gene interactive report as a pharmacogenetic interpretive service, and displaying said Type II report to said second user on said second graphical interface;

i) in response to said flag, billing said second user for said pharmacogenetic interpretive service, wherein said second user has preselected a payment method by entering a financial instrument at a paypoint associated with said second graphical user interface.

Optionally, said paypoint (typically paypoint 2) is configured for entering a financial instrument to be used as payment for said pharmacogenetic interpretive service. The financial instrument may be selected from insurance information, credit card information, on-line debit information, sponsored use access code, trial use access code, or subscription information.

In another embodiment of the conversion methods, conceived is a business method, as implemented on a computer host system, for obtaining automated third-party reimbursement by providing professional interpretation of a genetic testing result, comprising the steps of:

a) As a service to a client, said client having a customer, said client having provided a genetic test service for a patient on request of said customer,
 1) providing said client with a means for accessing a host system (20) at a first graphical user interface (30) and a means for entering a customer identifier and a genetic test result associated with the customer, and storing that information in a database on the host system;
 2) on command of the client, generating a test report for the client; the test result including i) a phenotypic interpretation of the genetic test result associated with that customer, ii) a list of drugs likely to be associated with an adverse drug reaction when administered to said patient, iii) a "sponsored user" hyperlink to a second graphical user interface, and iv) a password;
 3) on command of the client, securely transmitting the test report to the customer, said transmission constituting a service billable by the client to a third party payor;

b) when the customer accesses the "sponsored user" hyperlink and enters the password at a paypoint (2),
 1) providing the customer with direct access to an interactive webpage on the second graphical user interface (50) and allowing the customer to enter a plurality of clinical factors to be associated with the patient identifier and patient phenotype, including clinical factors selected from the group consisting of prescription drug(s) prescribed, bioactive substance(s) used, and clinical history factor(s),
 2) securely updating the interactive webpage with a prediction evaluating the biocompatibility between the clinical factors associated with the patient identifier and with the patient phenotype;
 3) displaying a warning of any predicted bioincompatibility; and,
 4) flagging the access as a billable service, and receiving reimbursement for the direct access to the system, and further receiving reimbursement from the client for access to the system.

In this latter conversion model, paypoint 2 is configured with a menu for choosing a method of payment selected from a) free trial period with authorization code, b) credit card payment for access, c) debit card information; d) entry of insurance information and on-line authorization from the insurer, e) subscription payment for access, f) sponsored use with authorization code, and g) wholesale group contract payment for access.

Unless the context requires otherwise, throughout the specification and claims which follow, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

While the above is a description of the preferred embodiments of the present invention, it is possible to use various alternatives, modifications and equivalents. Therefore, the scope of the present invention should be determined not with reference to the above description but should, instead, be determined with reference to the appended claims, along with their full scope of equivalents.

We claim:

1. A method for predicting a substance-factor interaction, which comprises:
  a) providing a graphical user interface, a host system, and a database, wherein said graphical user interface is configured for:
    i) accessing a patient record in said database, said patient record comprising a patient identifier and a first patient phenotype;
    ii) entering one or more factors into a list associated with said patient identifier, wherein said one or more factors are selected from the group consisting of prescription drug, substance, and personal characteristic;
  b) providing a predictive algorithm implemented on said host system, said algorithm having instructions for performing operations on said database, said patient record and said associated list, wherein said operations comprise:
    i) unbundling the list of factors, thereby forming an unbundled list;
    ii) selecting culprits from the unbundled list, where each culprit is a factor having the property of being an inhibitor or an inducer and retrieving from said database an intensity index INTX for each culprit, where intensity index INTX indicates relative strength of inhibition or induction by each culprit;
    iii) selecting victims from the unbundled list, where a victim is a factor having the property of being a metabolic substrate of one or more metabolic routes Rn;
    iv) identifying from said database each metabolic route associated with said sublist of victims;

v) identifying each interaction pair associated with said each metabolic route, each interaction pair consisting of a victim and a culprit;

vi) for each victim of said each interaction pair: calculating a CP score by multiplying an intensity index INTX associated with the culprit times a metabolic throughput proportion $R_{1/1-n}$, where $R_{1/1-n}$ is calculated as the metabolic throughput of said each metabolic route Rn divided by a sum of the throughput of all metabolic pathways acting on the victim in parallel;

vii) summing the CP scores for each victim and for each interacting pair, and tabulating the sums $\Sigma CP$;

viii) from the sums $\Sigma CP$, computing a change percent AUC for each victim and for each interacting pair;

ix) displaying a Type II report tabulating patient identifier, patient phenotype, factors entered in said list, and change % AUC for each victim; and, c) flagging the report as a billable service.

2. The method of claim 1, wherein said sublist of victims comprises a plurality of victims.

3. The method of claim 1, wherein said patient record comprises a plurality of patient phenotypes.

4. The method of claim 1, wherein said substance-factor interaction comprises a drug-gene interaction, a drug-drug interaction, or a combination thereof.

5. The method of claim 1, wherein said algorithm further comprises a subroutine, said subroutine having instructions for performing operations on said database, said patient record and said associated list, wherein said operations comprise:

i) accessing the database and identifying note or warnings compiled from published reports of an interaction between said first victim and said culprit;

ii) if no notes or warnings compiled, reporting said change percent AUC identified with said first victim and said culprit; and, iii) if notes or warnings compiled, reporting said notes or warnings identified with said first victim and said culprit.

6. The method of claim 1, wherein said operations further comprise:

i) for any prescription drug or substance on said list, accessing the database and identifying a class membership, wherein said class membership is defined by a side effect produced by all members of the class;

ii) for any class membership identified herein, accessing the database and identifying any factors from the list having said class membership in common; and, iii) reporting said factors in common, with a note advising that said side effect can be additive.

7. The method of claim 1, wherein said operations further comprise:

i) for any potential interaction pair for which said change percent AUC exceeds a threshold value, accessing said database and identifying a therapeutic class associated with said first victim;

ii) identifying an alternate member of said therapeutic class and calculating an alternate percent change AUC for the alternate member;

iii) reporting the alternate member in a listing a interactive selection of alternates if the alternate percent change AUC does not exceed a threshold value.

8. A method for predicting a drug-gene interaction, which comprises:

a) providing a graphical user interface, an host system, and a database, wherein said graphical user interface is configured for entering a patient record in said database, said record comprising a patient identifier and a first patient phenotype;

b) providing a predictive algorithm implemented on said host system, said algorithm having instructions for performing operations on said database, said patient record and a list of drugs in said database, wherein said operations comprise:

i) accessing said list of drugs in said database, said drugs comprising prescription drugs and substances, and unbundling the list, thereby compiling an unbundled list;

ii) determining an inhibition or an induction of at least one metabolic route Rn associated with said first phenotype; and assigning an intensity factor INTX to said inhibition or induction;

iii) selecting a sublist of victims from the unbundled list, where a victim is a member of said unbundled list having the property of being a metabolic substrate of said metabolic route Rn associated with said first phenotype;

iv) for each victim in said sublist, calculating a CP score by multiplying an intensity index INTX associated with inhibition or induction of said at least one metabolic route Rn associated with said first phenotype times a metabolic throughput proportion $R_{1/1-n}$, where $R_{1/1-n}$ is calculated as the metabolic throughput of said metabolic route Rn divided by a sum of the throughput of all metabolic pathways acting on the victim in parallel;

v) from the CP score of the preceding step, computing a change % AUC for each victim and for each interacting pair;

vi) discarding any drugs or substances in the sublist 4 for which the change % AUC is below a threshold value and forming a summary table;

vii) displaying a Type I report tabulating patient identifier, patient phenotype, laboratory identifier, and change % AUC for each drug or substance in said summary table; and, c) flagging the report as a billable service.

9. The method of claim 8, wherein said patient record comprises a plurality of patient phenotypes, and said operations comprise calculating a $\Sigma CP$ score for each victim, where said $\Sigma CP$ score is the sum of the CP scores over said plurality of phenotypes, and computing change % AUC for each victim from the $\Sigma CP$ score in said summary table.

10. The method for obtaining reimbursement for pharmacogenetic interpretive services, which comprises: a) implementing a billing server configured for detecting a flag associated with a billable service of claim 1; b) invoicing a payor associated with the patient identifier.

11. The method of claim 10, wherein said payor is a third party payor and said billing server comprises an insurance submodule.

12. The method for obtaining reimbursement for pharmacogenetic interpretive services, which comprises: a) implementing a billing server configured for detecting a flag associated with a billable service of claim 8; b) invoicing a payor associated with the patient identifier.

13. The method of claim 12, wherein said payor is a third party payor and said billing server comprises an insurance submodule.

14. A business method, as implemented on a computerized host system, for obtaining automated third-party reimbursement by providing pharmacogenetic interpretive services for preventing a possible adverse drug reaction, comprising the steps of:

a) providing a first user with a means for accessing a host system having a database and a means for entering a patient record comprising a patient identifier of a patient and a genotype associated with said patient identifier, and thereupon b) on command of said first user, translating said genotype into a phenotype and entering said phenotype in said patient record;

c) providing a second user with a means for entering a list of factors into the patient record, wherein the factors are selected from the group consisting of prescription drug(s) prescribed, substance(s) used, and clinical factor(s);

d) upon command of said second user, performing a predictive algorithm which comprises:
  i) unbundling the list of factors, thereby forming an unbundled list;
  ii) selecting culprits from the unbundled list, where each culprit is a factor having the property of being an inhibitor or an inducer, and retrieving from said database an intensity index INTX for each culprit, where intensity index INTX indicates relative strength of inhibition or induction by each culprit;
  iii) selecting victims from the unbundled list, where each victim is a factor having the property of being a metabolic substrate of one or more metabolic routes Rn;
  iv) identifying from said database each metabolic route associated with said sublist of victims;
  v) identifying each interaction pair associated with said each metabolic route, each interaction pair consisting of a victim and a culprit;
  vi) for each victim of said each interaction pair: calculating a CP score by multiplying an intensity index INTX associated with the culprit times a metabolic throughput proportion $R_{1/1-n}$, where $R_{1/1-n}$ is calculated as the metabolic throughput of said each metabolic route Rn divided by a sum of the throughput of all metabolic pathways acting on the victim in parallel;
  vii) summing the CP scores for each victim and for each interacting pair, and tabulating the sums $\Sigma CP$;
  viii) from the sums $\Sigma CP$, computing a change percent AUC for each victim and for each interacting pair, and computing a prediction warning of a potential bioincompatibility between said interacting pairs;

e) displaying a Type II report; and, f) flagging the prediction as a billable service, wherein the method is further characterized in that reimbursement is made according to a prearranged fee schedule between an operator of the host system and a third party payor contracted by said patient to pay for said billable service.

15. A business method, as implemented on a computerized host system, for obtaining automated third-party reimbursement by providing pharmacogenetic interpretive services for preventing a possible adverse drug reaction, comprising the steps of:

a) providing a first user with a means for accessing a host system and a means for entering a patient record comprising a patient identifier of a patient and a genotype associated with said patient identifier; and thereupon b) on command of said first user, translating said genotype into a phenotype and entering said phenotype in said patient record;

c) upon command of said first user, entering a list of drugs and performing a predictive algorithm which comprises:

i) accessing said list of drugs in said database, said drugs comprising prescription drugs and substances, and unbundling the list, thereby forming an unbundled list;
  ii) determining an inhibition or an induction of at least one metabolic route Rn associated with said first phenotype; and assigning an intensity factor INTX to said inhibition or induction;
  iii) selecting a sublist of victims from the unbundled list, where a victim is a member of said unbundled list having the property of being a metabolic substrate of said metabolic route Rn associated with said first phenotype;
  iv) for each victim of said sublist: calculating a CP score by multiplying an intensity index INTX associated with said first phenotype times a metabolic throughput proportion $R_{1/1-n}$, where $R_{1/1-n}$ is calculated as the metabolic throughput of said each metabolic route Rn divided by a sum of the throughput of all metabolic pathways acting on the victim in parallel;
  v) from the CP score of the preceding step, computing a change % AUC for each victim and for each interacting pair;
  vi) discarding any drugs or substances in the sublist for which the change % AUC is below a threshold value and forming a summary table;
  vii) displaying a Type I report tabulating patient identifier, patient phenotype, laboratory identifier, change % AUC for each drug or substance in said summary table; and a prediction warning of a potential interaction between said drug or substance and said phenotype, said report being a billable pharmacogenetic interpretive service;

d) upon command of said first user; transmitting said report to a customer, wherein said customer is a customer of said first user, and flagging said transaction to a billing server operated by said first user; and, e) receiving a reimbursement from said first user for access to said host system; wherein the method is further characterized in that the billing server operated by said first user automatically bills for said pharmacogenetic interpretive service.

16. The business method of claim 15, further characterized in that said billing server automatically bills a third party payor contracted by said patient to pay for said pharmacogenetic interpretive service.

17. A business apparatus for obtaining automated reimbursement for pharmacogenetic interpretive services, said apparatus comprising a computerized host system operated by a host system operator and having a means for data storage, a database, a means for data processing, a means for networking, a first graphical user interface for access to the host system by a first user, a second graphical interface for access to the host system by a second user, wherein said apparatus is configured with means for:

a) under control of said first user, entering and storing a laboratory identifier, patient identifier and a genetic test result comprising a patient genotype in a patient record on said first graphical user interface of said host system, said first user being a laboratory with a client relationship with said host system operator;

b) on command of said first user, performing a phenotypic interpretation of said genotype entering said phenotype in said patient record on said host system;

c) on command of said first user, using a first predictive algorithm resident in said host system to prepare a predictive drug-gene interaction report, said first predictive algorithm comprising:
  i) accessing a said list of drugs on a said database, said drugs comprising prescription drugs and substances, and unbundling the list, thereby compiling an unbundled list;
  ii) determining an inhibition or an induction of at least one metabolic route Rn associated with said first phenotype; and assigning an intensity factor INTX to said inhibition or induction;
  iii) selecting from the unbundled list a sublist of victims from the unbundled list, where a victim is a member of said unbundled list having the property of being a metabolic substrate of said metabolic route Rn associated with said first phenotype;
  iv) for each victim in said sublist, calculating a CP score by multiplying an intensity index INTX associated said with inhibition or induction of said at least one metabolic route Rn associated with said first phenotype times a metabolic throughput proportion $R_{1/1-n}$, where $R_{1/1-n}$ is calculated as the metabolic throughput of said metabolic route Rn divided by a sum of the throughput of all metabolic pathways acting on the victim in parallel;
  v) from the CP score of the preceding step, computing a change % AUC for each victim and for each interacting pair;
  vi) discarding any drugs or substances in the sublist for which the change % AUC is below a threshold value and forming a summary table;
  vii) displaying a Type I report tabulating patient identifier, patient phenotype, laboratory identifier, change % AUC for each drug or substance in said summary table; and a prediction warning of a potential interaction between said drug or substance and said phenotype, said report being a billable pharmacogenetic interpretive service;
d) under control of said host system operator, appending a hyperlink to said predictive drug-gene interaction report, said hyperlink having the property of linking to said second graphical user interface;
e) on command of said first user, transmitting said predictive drug-gene interaction report with appended hyperlink to said second user, said second user being a patient or a responsible medical care provider;
f) under control of said second user, opening said second graphical user interface when said second user accesses said appended hyperlink;
g) under control of said second user, editing said patient record to add a list of factors to be associated with said patient identifier, wherein said factors are selected from the group consisting of prescription drug, substance, and clinical factor;
h) on command of said second user, using a second predictive algorithm resident in said host system to prepare a predictive drug-drug and drug-gene interactive report, said second predictive algorithm comprising:
  i) unbundling the list of factors, thereby forming an unbundled list;
  ii) selecting culprits from the unbundled list, where each culprit is a factor having the property of being an inhibitor or an inducer, and retrieving from said database an intensity index INTX for each culprit, where intensity index INTX indicates relative strength of inhibition or induction by each culprit;
  iii) selecting victims from the unbundled list, where each victim is a factor having the property of being a metabolic substrate of one or more metabolic routes Rn;
  iv) identifying from said database each metabolic route associated with said sublist of victims;
  v) identifying each interaction pair associated with said each metabolic route, each interaction pair consisting of a victim and a culprit;
  vi) for each victim of said each interaction pair: calculating a CP score by multiplying an intensity index INTX associated with the culprit times a metabolic throughput proportion $R_{1/1-n}$, where $R_{1/1-n}$ is calculated as the metabolic throughput of said each metabolic route Rn divided by a sum of the throughput of all metabolic pathways acting on the victim in parallel;
  vii) summing the CP scores for each victim and for each interacting pair, and tabulating the sums $\Sigma CP$;
  viii) from the sums $\Sigma CP$, computing a change percent AUC for each victim and for each interacting pair, and computing a prediction warning of a potential bioincompatibility between said interacting pairs;
  ix) displaying a Type II report tabulating patient identifier, patient phenotype, factors entered in said list, and change % AUC for each victim on said second graphical interface; and,
i) flagging as a billable pharmacogenetic interpretive service; and
j) in response to said flag, billing said second user for said pharmacogenetic interpretive service, wherein said second user has preselected a payment method by entering a financial instrument at a paypoint associated with said second graphical user interface.

18. The business apparatus of claim 17, wherein said paypoint is configured for entering a financial instrument to be used as payment for said pharmacogenetic interpretive service.

19. The business apparatus of claim 18, wherein said financial instrument is selected from insurance information, credit card information, on-line debit information, sponsored use access code, trail use code, or subscription information.

20. The business apparatus of claim 19 wherein said payment is configured with a menu for choosing a method of payment selected from a) free trial period with authorization code, b) credit card payment for access, c) debit card information; d) entry of insurance information and on-line authorization from the insurer, e) subscription payment for access, f) sponsored use with authorization code, and g) wholesale group contract payment for access.

* * * * *